(12) United States Patent
Politis et al.

(10) Patent No.: US 10,342,918 B2
(45) Date of Patent: Jul. 9, 2019

(54) SUBCUTANEOUS INFUSION DEVICE

(75) Inventors: Victor Politis, Framingham, MA (US); Gary M. Searle, Norfolk, MA (US); Mark Guarraia, Cranston, RI (US); Joseph Gordon, Mansfield, MA (US); Dave Zitnick, Pawtucket, RI (US); Sharon Mulligan, Pawtucket, RI (US); Ralph L. Sonderegger, Farmington, UT (US); Thomas G. Kluck, Washingtonville, NY (US); Joshua D. Horvath, Sparta, NJ (US); Charles G. Hwang, Wellesley, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 398 days.

(21) Appl. No.: 13/984,029

(22) PCT Filed: Feb. 8, 2012

(86) PCT No.: PCT/US2012/000069
§ 371 (c)(1),
(2), (4) Date: Nov. 15, 2013

(87) PCT Pub. No.: WO2012/108955
PCT Pub. Date: Aug. 16, 2012

(65) Prior Publication Data
US 2014/0058353 A1 Feb. 27, 2014

Related U.S. Application Data

(60) Provisional application No. 61/441,265, filed on Feb. 9, 2011.

(51) Int. Cl.
*A61M 5/142* (2006.01)
*A61M 5/158* (2006.01)

(52) U.S. Cl.
CPC ........ *A61M 5/14248* (2013.01); *A61M 5/158* (2013.01); *A61M 2005/14252* (2013.01); *A61M 2005/1585* (2013.01)

(58) Field of Classification Search
CPC ........ A61M 5/158; A61M 2005/14252; A61M 2005/14256; A61M 2005/14284;
(Continued)

(56) References Cited

U.S. PATENT DOCUMENTS 3,918,355 A 11/1975 Weber et al.
5,129,884 A 7/1992 Dysarz
(Continued)

FOREIGN PATENT DOCUMENTS

EP 2495001 A1 9/2012
JP 2005526560 A 9/2005
(Continued)

*Primary Examiner* — Nathan R Price
*Assistant Examiner* — Weng Lee
(74) *Attorney, Agent, or Firm* — Dickinson Wright, PLLC

(57) ABSTRACT

An infusion system having an integrated inserter and infusion set (10) for containing and placing a flexible catheter (40), and a retractable introducer needle (26), wherein the catheter (40) is isolated from movement after placement. The integrated inserter and infusion set (10) includes a hub (20), having a user push button (30) to activate the device for catheter (40) placement. An adhesive liner (34) can be provided to cover an adhesive layer (36), such as pressure sensitive adhesive (PSA), on the bottom of the device (10).

8 Claims, 33 Drawing Sheets

(58) Field of Classification Search
CPC .. A61M 2005/1583; A61M 2005/1585; A61M 2039/0232
USPC .............. 604/136, 156, 157, 164.01, 164.04, 604/167.01, 167.02, 506
See application file for complete search history.

(56) References Cited

U.S. PATENT DOCUMENTS

| | | | |
|---|---|---|---|
| 6,485,461 | B1 | 11/2002 | Mason et al. |
| 6,699,218 | B2 | 3/2004 | Flaherty et al. |
| 7,128,727 | B2 | 10/2006 | Flaherty et al. |
| 7,137,964 | B2 | 11/2006 | Flaherty |
| 7,144,384 | B2 | 12/2006 | Gorman et al. |
| 7,303,549 | B2 | 12/2007 | Flaherty et al. |
| 7,455,663 | B2 | 11/2008 | Bikovsky |
| 7,682,338 | B2 | 3/2010 | Griffin |
| 9,119,913 | B2 | 9/2015 | Lanigan |
| 9,402,950 | B2 | 8/2016 | Dilanni et al. |
| 2002/0022855 | A1 | 2/2002 | Bobroff et al. |
| 2002/0040208 | A1 | 4/2002 | Flaherty et al. |
| 2004/0010207 | A1 | 1/2004 | Flaherty et al. |
| 2004/0162521 | A1 | 8/2004 | Bengtsson |
| 2005/0171512 | A1 | 8/2005 | Flaherty |
| 2005/0203461 | A1* | 9/2005 | Flaherty ............ A61M 5/14248 604/131 |
| 2006/0142698 | A1 | 6/2006 | Ethelfeld |
| 2007/0093754 | A1 | 4/2007 | Mogensen et al. |
| 2007/0219496 | A1 | 9/2007 | Kamen et al. |
| 2007/0228203 | A1* | 10/2007 | Ruff ..................... B60R 22/405 242/383.2 |
| 2008/0195045 | A1 | 8/2008 | Lanigan |
| 2008/0249473 | A1 | 10/2008 | Rutti et al. |
| 2008/0312558 | A1 | 12/2008 | Krulevitch et al. |
| 2008/0312588 | A1 | 12/2008 | Faccioli et al. |
| 2009/0012472 | A1 | 1/2009 | Ahm et al. |
| 2009/0062767 | A1 | 3/2009 | Van Antwerp et al. |
| 2009/0099521 | A1 | 4/2009 | Gravesen et al. |
| 2009/0198215 | A1* | 8/2009 | Chong ................ A61M 5/1413 604/506 |
| 2009/0254041 | A1 | 10/2009 | Krag et al. |
| 2009/0306596 | A1 | 12/2009 | Mogensen et al. |
| 2010/0100077 | A1 | 4/2010 | Rush et al. |
| 2010/0274112 | A1 | 10/2010 | Hoss et al. |
| 2010/0286714 | A1* | 11/2010 | Gyrn .................... A61M 5/158 606/139 |
| 2011/0054285 | A1 | 3/2011 | Searle et al. |
| 2011/0054390 | A1 | 3/2011 | Searle et al. |
| 2011/0313357 | A1 | 12/2011 | Skutnik et al. |
| 2012/0010642 | A1* | 1/2012 | Lee .................... A61B 5/15194 606/182 |
| 2014/0142508 | A1 | 5/2014 | Dilanni et al. |
| 2017/0128664 | A1 | 5/2017 | Dilanni et al. |

FOREIGN PATENT DOCUMENTS

| | | |
|---|---|---|
| JP | 2006501878 A | 1/2006 |
| JP | 2006527036 A | 11/2006 |
| JP | 2008528086 A | 7/2008 |
| JP | 2008220961 | 9/2008 |
| JP | 2009106749 A | 5/2009 |
| JP | 2009525822 A | 7/2009 |
| JP | 2009539444 A | 11/2009 |
| JP | 2010501281 A | 1/2010 |
| JP | 2010517700 A | 5/2010 |
| JP | 2010525869 A | 7/2010 |
| JP | 2010533525 A | 10/2010 |
| JP | 2010534530 A | 11/2010 |
| WO | WO-9620021 A1 | 7/1996 |
| WO | WO-02066093 A2 | 8/2002 |
| WO | WO-2004006982 A2 | 1/2004 |
| WO | WO-2004101071 A2 | 11/2004 |
| WO | WO-2006077262 A1 | 7/2006 |
| WO | WO-2008133702 A1 | 11/2008 |
| WO | WO-2008155377 A1 | 12/2008 |
| WO | WO-2009039013 A1 | 3/2009 |
| WO | WO-2012141759 A1 | 10/2012 |

\* cited by examiner

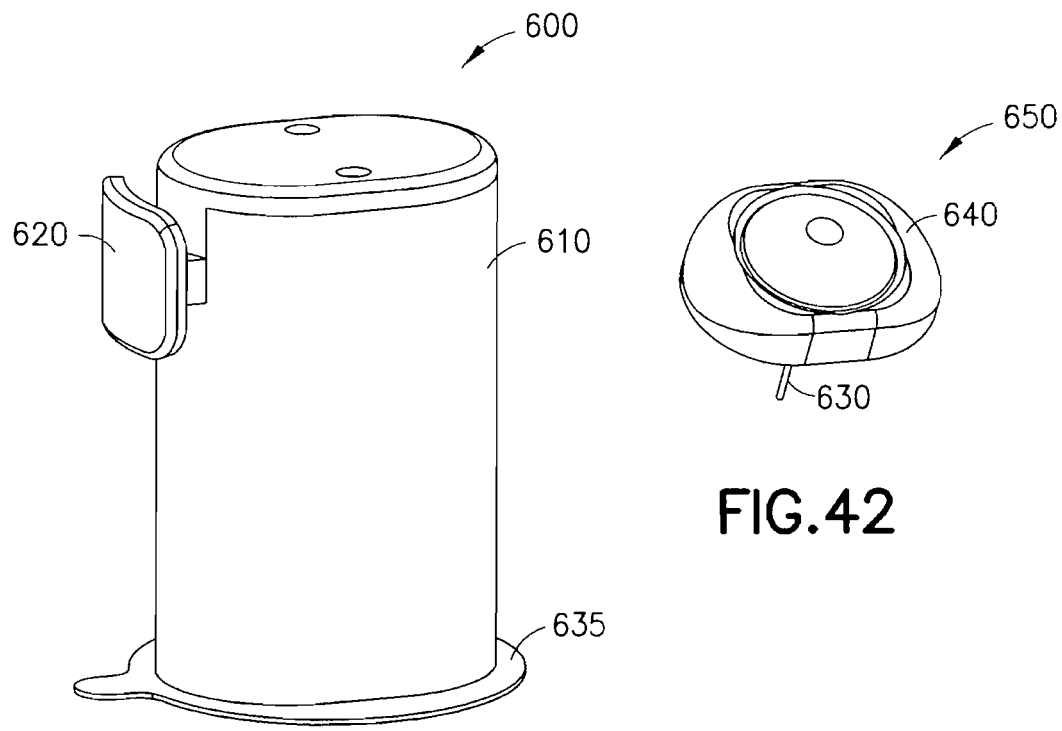
FIG.41
FIG.42
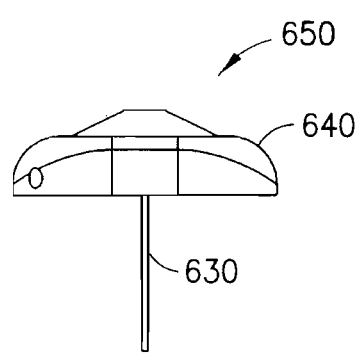
FIG.43
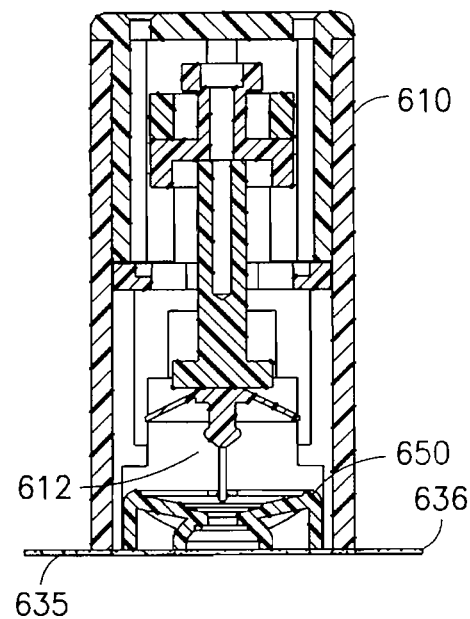
FIG.44

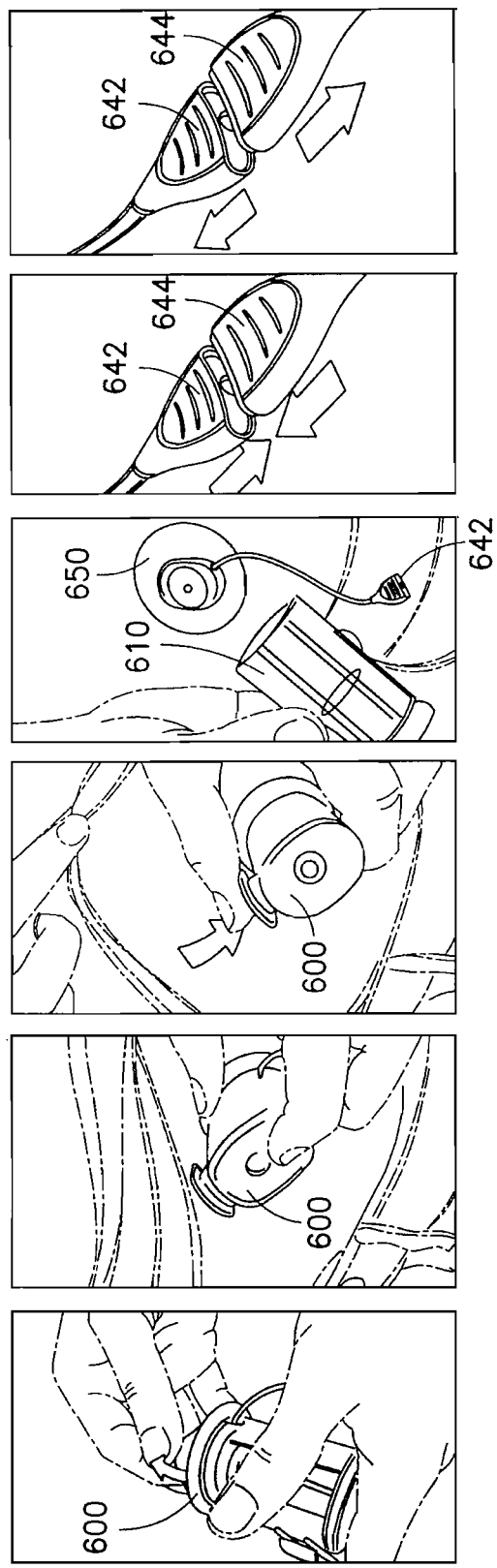

SUBCUTANEOUS INFUSION DEVICE

CROSS-REFERENCE TO RELATED APPLICATIONS

This application claims the benefit under 35 U.S.C. § 119(e) of a U.S. provisional patent application of Victor Politis et al. entitled "Subcutaneous Infusion Device", Ser. No. 61/441,265, filed on Feb. 9, 2011, the entire content of said application being incorporated herein by reference.

FIELD OF THE INVENTION

The present invention relates generally to insulin infusion systems, specifically an integrated inserter and infusion set for containing and placing a cannula, a pre-loaded inserter and infusion set for containing and placing a flexible catheter, and an inserter for containing and placing an infusion set with a retractable introducer needle, and wherein the catheter is isolated from movement after placement.

BACKGROUND OF THE INVENTION

A large number of people, including those suffering from conditions such as diabetes, use some form of infusion therapy, such as daily insulin infusions, to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or a flexible cannula extends. The hub or base has an adhesive which retains the base on the skin surface during use, which may be applied to the skin manually or with the aid of a manual or automatic insertion device. Often, a user is further required to carry and provide a separate inserter. Accordingly, this method of treatment can become cumbersome and wasteful when dealing with the large number of required components.

Many infusion sets use a soft, Teflon-based cannula (also referred to as a catheter) to infuse insulin under the skin surface. Such Teflon cannulas are associated with less discomfort than steel cannulas. However, soft cannulas are prone to kink, which can delay or interrupt the patient's insulin delivery and reduce therapy. Most soft cannula infusion sets are inserted using a steel introducer needle that is positioned inside the cannula lumen and which extends beyond the cannula to initiate penetration. The introducer needle is then removed after catheter insertion.

Some infusion sets also use a separate high-impact, spring-loaded inserter that propels the introducer needle and cannula into the tissue at a desired speed, and to a desired depth. This process results in numerous steps which can be required to insert the infusion set, since it often requires the user to carry a separate insertion device, and load a set into the insertion device each time. The separate insertion device or inserter is therefore an added cost to the user and the additional steps of properly loading a device or set in the separate insertion device can become cumbersome.

As noted, most insulin infusion sets deliver medicament to the subcutaneous layers of skin using either rigid metal needles or flexible plastic cannulas. However, most insulin infusion sets do not provide any features to isolate the inserted needle or cannula from shock or other external forces. Also, as noted above, most insulin sets require separate inserters, which require the user to carry extra components for treatment. In regard to such separate inserters, an additional problem encountered by users of such separate inserters is the need to carry additional accessories and the difficulty of loading the infusion set onto the insertion device at each use.

Still further, in a conventional system, an introducer needle, catheter, and adhesive are all deployed at substantially the same time when inserted. During such "ballistic" insertion, there is a high-speed contact of the adhesive pad while the introducer needle and the catheter are being inserted, which may result in partially inserted catheters and/or incomplete adhesion.

Accordingly, a need exists for improved infusion sets that can deliver content to the subcutaneous skin layer while maintaining a degree of comfort to the user.

SUMMARY OF THE INVENTION

An object of the present invention is to provide an integrated inserter and infusion set for containing and placing a catheter, while maintaining a degree of comfort to the user.

Another object of the present invention is to provide an integrated inserter and infusion set for containing and placing a flexible catheter.

Another object of the present invention is to provide a pre-loaded inserter for containing and placing an infusion set with a retractable introducer needle, wherein the catheter is isolated from movement after placement.

Another object of the present invention is to provide a device to place a catheter of an infusion set such that a user can attach the complete device to the skin surface and then deploy the catheter, thereby preventing any bunching of the adhesive when attached, as well as ensuring that the set hub is fully contacting the skin before the introducer needle is inserted.

Another object of the present invention is to provide a device to place a cannula or catheter of an infusion set such that the catheter is inserted at the correct depth.

Another object of the present invention is to provide a device to contain and place a catheter of an infusion set and retract the introducer needle back into the catheter by a short distance, to thereby provide structural support to the catheter and prevent kinking as well as shielding the surrounding tissue from the sharp introducer needle tip.

Another object of the present invention is to provide a device to contain and place a catheter of an infusion set using an automatic method of deployment such that the user only needs to push down the top of the device, such as a button disposed at or near the top of the device, to insert both the introducer needle and the catheter.

Another object of the present invention is to provide a pre-loaded device to contain and place a catheter of an infusion set using an automatic method of deployment such that the user only needs to push down the top of the device, such as a button disposed at or near the top of the device, to further activate the introducer needle retraction operation.

Another object of the present invention is to provide a device to contain and place a catheter of an infusion set such that partial retraction of the introducer needle back into the catheter after the catheter of the infusion set is inserted provides structural integrity while maintaining the desirable biocompatibility aspects of the soft catheter.

Another object of the present invention is to provide a device to contain and place a catheter of an infusion set using a stronger, more flexible catheter that prevents kinking as it is much stiffer than a conventional Teflon catheter.

Another object of the present invention is to provide a device to contain and place a catheter of an infusion set such that the introducer needle is hidden from the user prior to use and insertion, which makes the device more safe and appealing to users who are uncomfortable with needles.

Another object of the present invention is to provide a device to contain and place a catheter of an infusion set such that the catheter assembly is configured to "float" in the hub, which serves to isolate the catheter from external forces once in place and to dampen motion due to body movement or accidental bumps and/or tubing tugs.

These and other objects are substantially achieved by providing an integrated inserter and infusion set for containing and placing a cannula, an integrated inserter and infusion set for containing and placing a flexible catheter, and a pre-loaded inserter for containing and placing an infusion set with a retractable introducer needle, wherein the catheter is isolated from movement after placement.

BRIEF DESCRIPTION OF THE DRAWINGS

The various objects, advantages and novel features of exemplary embodiments of the present invention will be more readily appreciated from the following detailed description when read in conjunction with the appended drawings, in which:

FIGS. 41-43 are views of an exemplary device utilizing a pre-loaded inserter and infusion set in accordance with an eighth embodiment of the present invention;

FIG. 44 is a cross-sectional view of the exemplary device of FIG. 41, illustrating the components thereof in greater detail;

FIGS. 46A-46F are views of the exemplary device of FIG. 41 in use.

Throughout the drawings, like reference numerals will be understood to refer to like parts, components and structures.

DETAILED DESCRIPTION OF THE EXEMPLARY EMBODIMENTS

Figure 1:
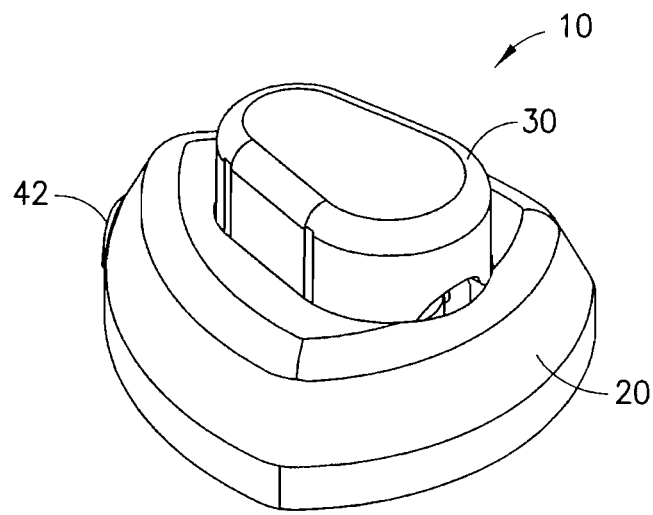
FIG. 1 is a perspective view of an exemplary device utilizing an integrated inserter and set in accordance with a first embodiment of the present invention before deployment.
Figure 2:
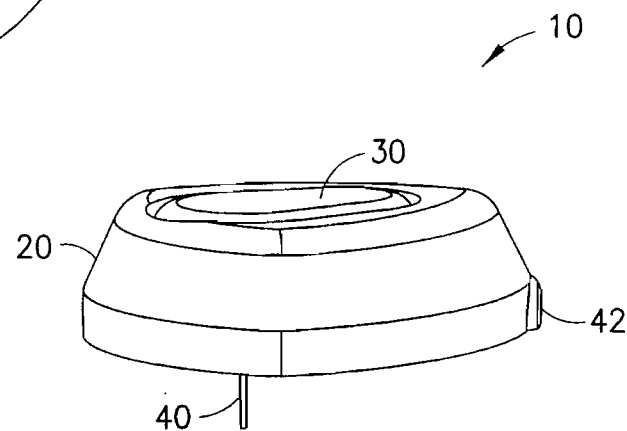
FIG. 2 is a perspective view of the exemplary device of FIG. 1 after deployment.
Figure 3:
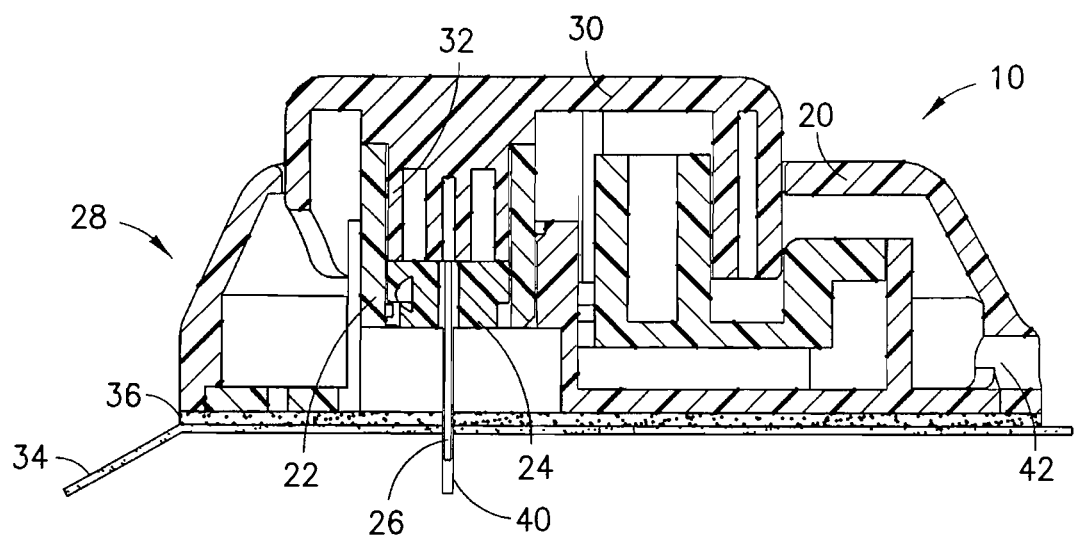
FIG. 3 is a cross-sectional view of the exemplary device of FIG. 1, illustrating the components thereof in greater detail.

In a first exemplary embodiment of the present invention, the device comprises an infusion set and insertion device integrated into a single unit, thereby eliminating the need to carry any additional accessories and avoid the difficulty associated with loading the infusion set onto the insertion device at each use. FIG. 1 is a perspective view of an exemplary device 10 utilizing an integrated inserter and set in accordance with a first embodiment of the present invention before deployment, and FIG. 2 is a perspective view of the exemplary device of FIG. 1 after deployment. The device 10 comprises a hub 20, having a user push button 30 to activate the device for catheter placement. As shown in FIG. 2, a catheter 40 can be extended from a bottom surface of the hub 20 during activation of the device. FIG. 3 is a cross-sectional view of the exemplary device of FIG. 1, illustrating the components thereof in greater detail.

As shown in FIG. 3, the hub 20 comprises an opening at a top surface and in which the push button 30 is disposed. The push button 30 is configured to slidably travel downward, substantially perpendicular to the skin surface, from an extended position as shown in FIG. 1 to a substantially flush position shown in FIG. 2. An outer dimension of the push button 30 is configured to be slidably received in a similar shaped opening in the top of the hub 20. In the exemplary embodiment shown, both the hub 20 and the push button 30 have a non-circular shape, but are not limited thereto. In an exemplary embodiment, the non-circular shape can be configured to facilitate offsetting the position of the catheter to one side of the device, resulting in less material where a viewing window can be located.

The hub 20 is configured to position the catheter and introducer needle offset to one side of the device 10, near a viewing window 28 provided in the housing of the hub 20. The viewing window 28 can be provided as an opening in the hub 20, or as a clear and/or magnifying material to allow the user or others to view and monitor conditions of the insertion site such as redness and/or bleeding that can occur during use and which may require attention.

The hub 20 further comprises a tube connection port 42 to which an exemplary tube 44 can be connected to connect the infusion set with a medicament pump or other supply vessel.

An adhesive liner 34 can be provided to cover an adhesive layer 36, such as pressure sensitive adhesive (PSA), on the bottom of the device 10.

The push button 30 comprises at least one projection 32 on a lower surface to slidably engage a similar opening 22 in the hub 20. In doing so, the push button 30 is configured to press a needle septum 24 and introducer needle 26 toward an insertion site when pressed by a user. The introducer needle 26 enters and guides the catheter 40 for insertion and placement. As shown in FIG. 3, the introducer needle 26 tip can then be retracted a slight distance back into the catheter 40. That is, the push button 30 is configured to move back up a small distance once the device is activated and to retract the introducer needle 26 with it. In an exemplary embodiment, the engagement between projection 32 and opening 22 can be configured to have a portion at an end stroke of the button 30 that biases the button 30 upward, to thereby retract the button 30 slightly when the user stops pressing the button 30. This can be achieved by creating tapers or other engagement features to bias the button 30 or bias the needle septum 24 towards slight retraction when downward pressure on the button 30 is released. The partial retraction of the introducer needle 26 back into the catheter 40 after the catheter 40 of the device 10 is inserted provides structural integrity while maintaining the desirable biocompatibility aspects of the soft catheter 40. Further, the tissue is shielded from the sharp introducer needle tip to reduce irritation at the infusion site.

Figure 4C:
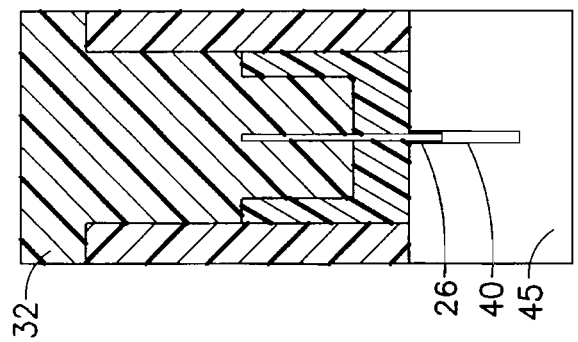
FIGS. 4A-4C are enlarged cross-sectional views of the exemplary device of FIG. 1 illustrating the relation between the introducer needle and catheter during use.
Figure 4B:
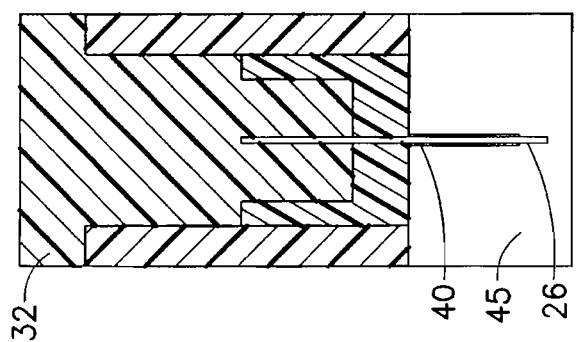
Figure 4A:
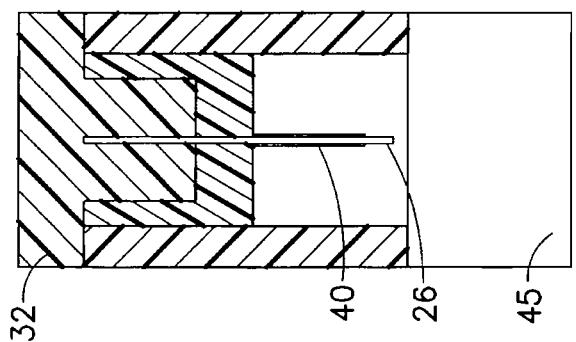

FIGS. 4A-4C are enlarged cross-sectional views of the exemplary device 10 of FIG. 1 illustrating the relation between the introducer needle 26 and catheter 40 during use. In a first position prior to activation in FIG. 4A, the introducer needle 26 is disposed within an inner lumen of the catheter 40 and extends slightly at the exposed tip thereof. The introducer needle 26 and catheter 40 are contained within the set as permitted by the button 30 in the pre-activation position. As the button 30 and is pressed and projection 32 of the button 30 moves downward, the needle septum 24, introducer needle 26, and catheter 40 are all advanced toward the insertion site until seated in a skin surface 45 as shown in FIG. 4B. Once in place, the introducer needle 26 is retracted slightly back into the catheter 40 (e.g., by about 1-3 mm) as shown in FIG. 4C. The engagement between projection 32 and opening 22 is configured to have a portion at an end stroke of the button 30 that biases the button 30 to retract slightly when the user stops pressing the button 30. As noted above, the partial retraction of the introducer needle 26 back into the catheter 40 after the catheter 40 of the device 10 is inserted provides structural integrity while maintaining the desirable biocompatibility aspects of the soft catheter 40, and the tissue is shielded from the sharp introducer needle tip to reduce irritation at the infusion site.

Figure 5C:
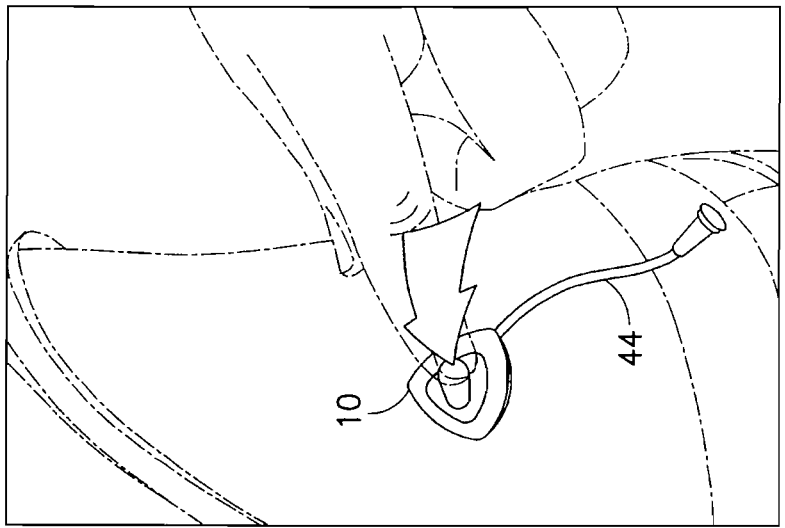
FIGS. 5A-5C are views of the exemplary device of FIG. 1 in use.
Figure 5B:
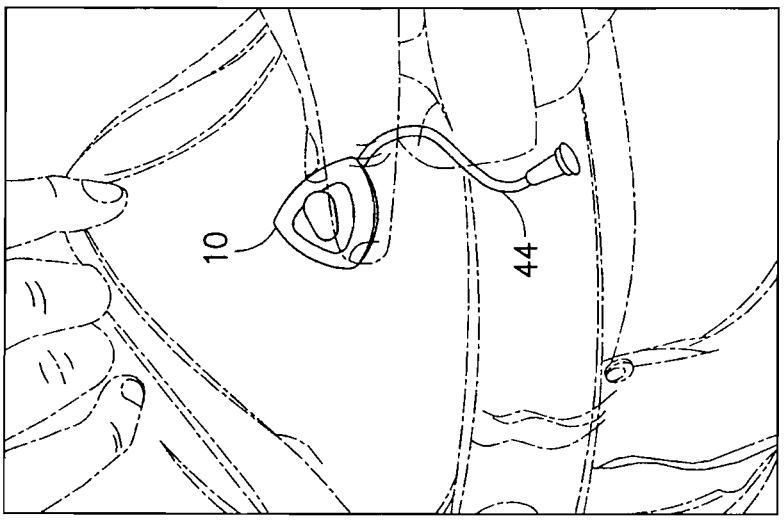
Figure 5A:
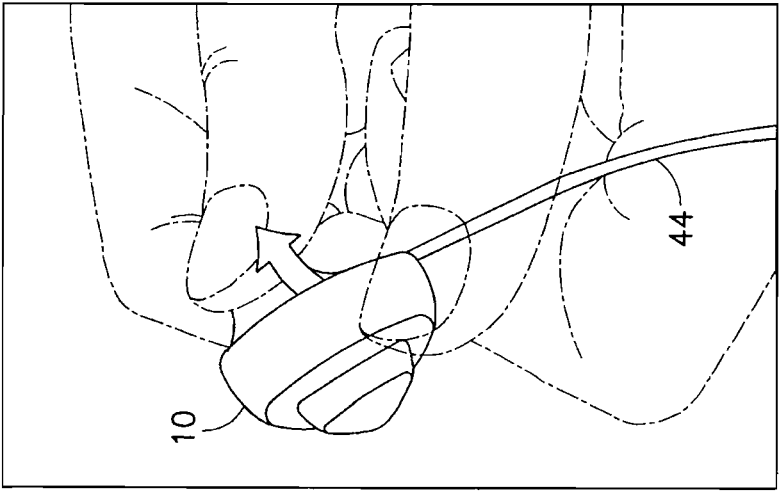

FIGS. 5A-5C are views of the exemplary device 10 of FIG. 1 in use. In a first step of FIG. 5A, a user removes the adhesive liner from the lower surface to expose the adhesive layer 36 on the bottom of the device 10. The hub 20 of the device 10 is then secured to an infusion site using the exposed adhesive layer 36 as shown in FIG. 5B. This ensures that the hub 20 of the device 10 is fully contacting and adhesively secured to the skin surface before the user performs the deployment of the introducer needle 26 and catheter 40. The user then presses the top button 30 of the device 10 to insert the introducer needle 26 and catheter 40 in a single motion as shown in FIG. 5C. The button 30 then retracts slightly when the user stops pressing the button 30 resulting in a partial retraction of the introducer needle 26 back into the catheter 40. The tube 44 can then be connected to a pump or other medicament supply.

In the first exemplary embodiment of the present invention, the user can attach the complete device to the skin surface and deploy the catheter of the infusion set, preventing any bunching of the adhesive when attached, as well as ensuring that the set hub is fully contacting and adhesively secured to the skin before the introducer needle and catheter are inserted. This also ensures that the catheter is inserted at the correct depth. The exemplary device then functions to retract the introducer needle back into the catheter a short distance, to thereby provide structural support to the catheter which prevents kinking as well as shielding the surrounding tissue from the sharp introducer needle tip. The device uses a manual method of deployment as the user is required to push down the top of the device, such as a button disposed at or near the top of the device, to insert both the introducer needle and the catheter. Such an action can further activate the introducer needle retraction operation.

In a conventional system, an introducer needle, catheter, and adhesive, are all deployed at substantially the same time. During such ballistic insertion, there is a high-speed contact of the adhesive pad while the introducer needle and the catheter are being inserted which may result in partially inserted catheters and/or incomplete adhesion. The exemplary first embodiment of the present invention eliminates the potential of partial insertion of the catheter and/or incomplete adhesion, since the system and method first ensures that the hub of the set is fully contacting and adhesively secured to the skin surface, and then performs the deployment of the introducer needle and catheter with full control as the user pushes the catheter and introducer needle both into the skin using a manual push button operation. Release of the button permits the partial retraction of the introducer needle back into the catheter after the catheter of the infusion set is inserted to provide structural integrity while maintaining the desirable biocompatibility aspects of the soft catheter. In doing so, the tissue is shielded from the sharp introducer needle tip to reduce irritation at the infusion site.

The exemplary first embodiment of the present invention significantly reduces the steps required to insert the catheter of the infusion set since the user is not required to load an infusion set into an inserter device. Further, the introducer needle is hidden from the user prior to use and insertion which makes the device more safe and appealing to users who are uncomfortable with needles.

As noted above, the exemplary first embodiment of the present invention is configured to allow the user to attach the device to the skin surface in a first step, deploy the introducer needle and catheter in a second step thereby preventing any bunching of the adhesive when attached as well as ensuring that the set hub is fully contacting and adhesively secured to the skin before the introducer needle is inserted, and retract the introducer needle slightly in a third step by releasing the button. This also ensures that the catheter is inserted at the correct depth. Further, since the catheter and the introducer needle are preferably offset to one side of the device, the viewing window allows the user or others to view and monitor conditions of the insertion site such as redness and/or bleeding that can occur during use and which may require attention.

In a second exemplary embodiment of the present invention, the device comprises another infusion set and insertion device integrated into a single unit, thereby again eliminating the need to carry any additional accessories and avoid the difficulty associated with loading the infusion set onto the insertion device at each use.

Figure 6:
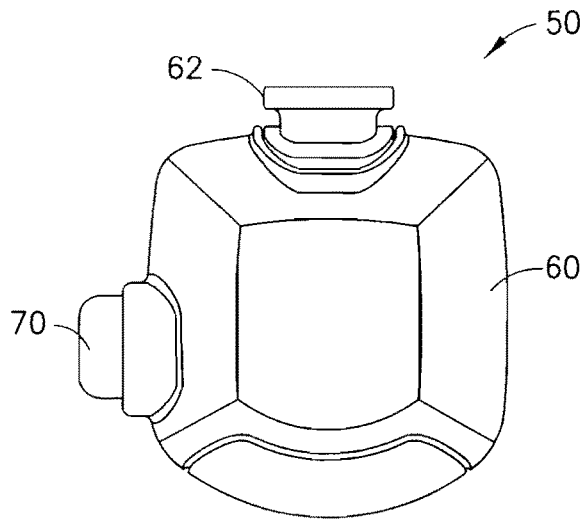
FIGS. 6 and 7 are views of an exemplary device utilizing an integrated inserter and infusion set in accordance with a second embodiment of the present invention.
Figure 7:
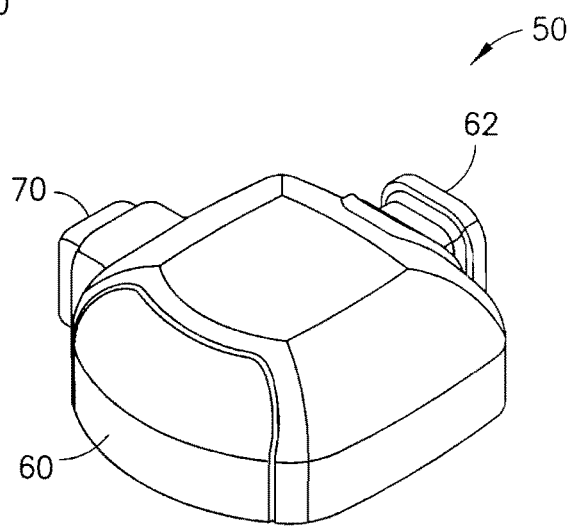
Figure 8:
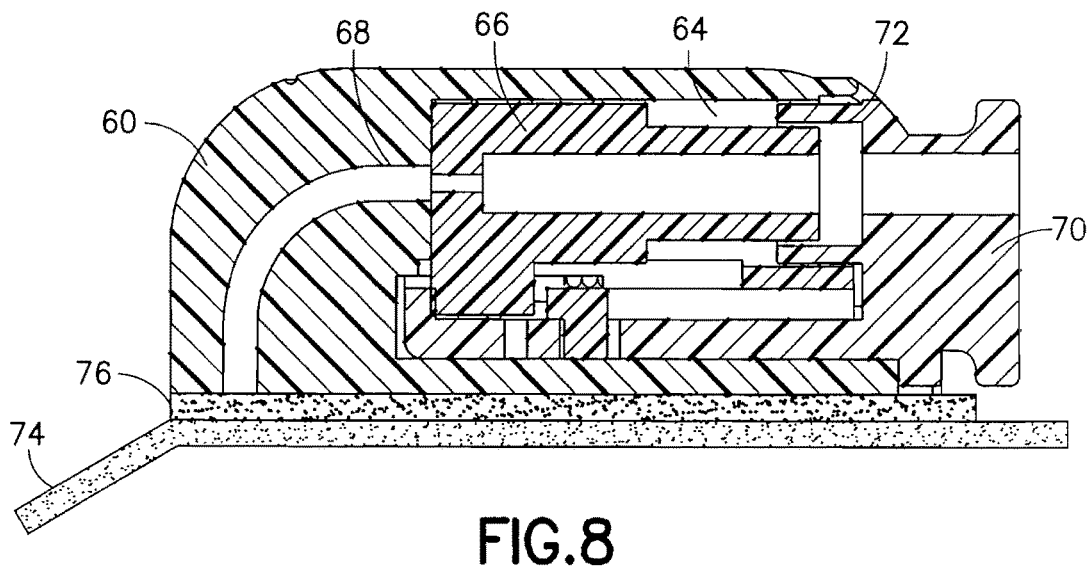
FIG. 8 is a cross-sectional view of the exemplary device of FIG. 6, illustrating the components thereof in greater detail.
Figure 9:
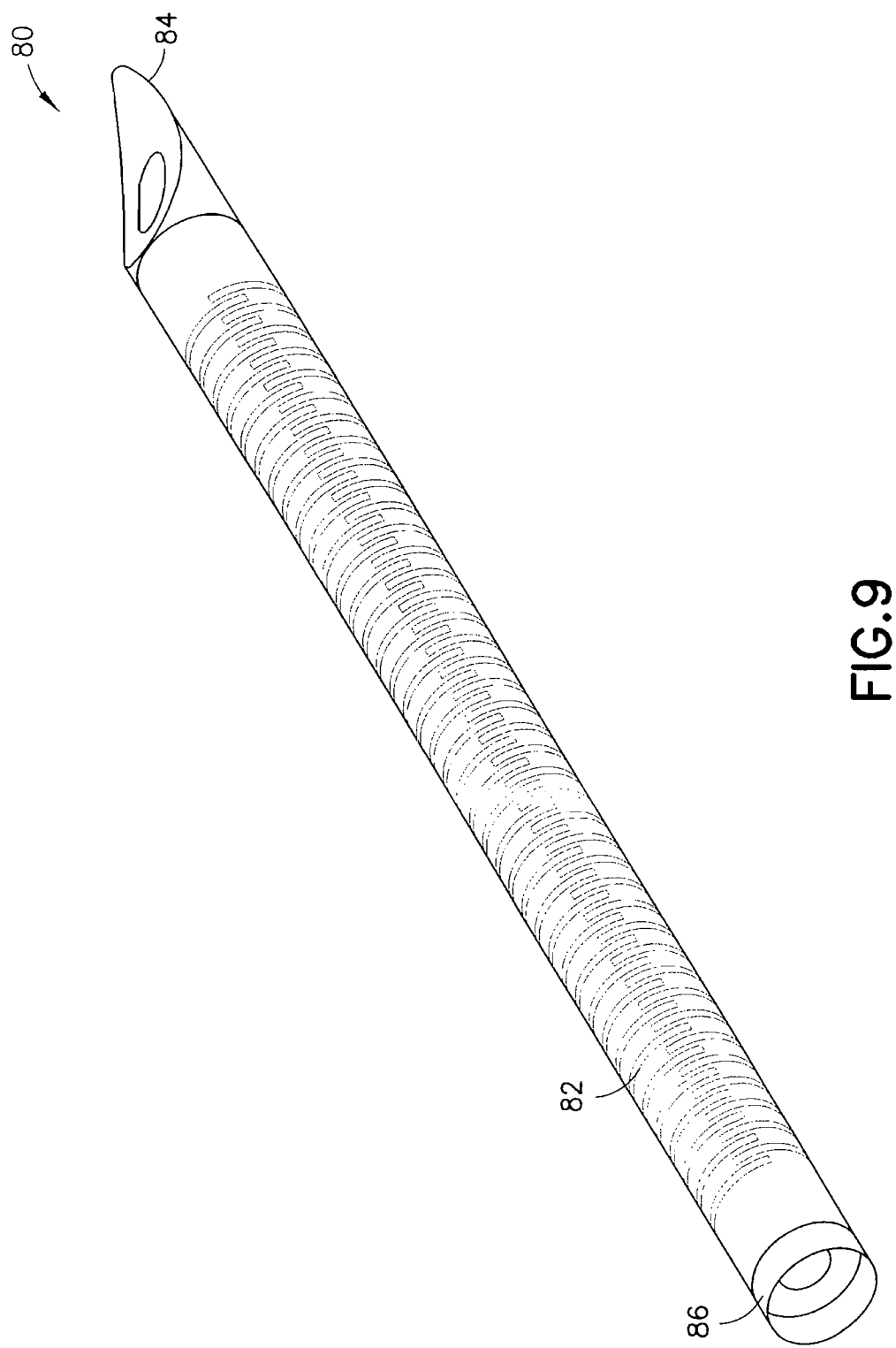
FIG. 9 is an enlarged, perspective view of an exemplary flexible catheter.

FIGS. 6 and 7 are views of an exemplary device 50 utilizing an integrated inserter and set in accordance with a second embodiment of the present invention. The device 50 comprises a hub 60, from which a user push button 70 extends. An in-dwelling, flexible cannula 80 can be extended from a bottom surface of the hub 60 during activation of the device. FIG. 8 is a cross-sectional view of the exemplary device of FIG. 6, illustrating the components thereof in greater detail. FIG. 9 is a view of the exemplary in-dwelling cannula 80 used in this embodiment, comprising a flexible, skin-piercing needle or catheter that does not require a separate introducer needle.

As shown in FIG. 8, the hub 60 comprises an opening at a side surface and in which the push button 70 is disposed. The push button 70 is configured to slidably travel substantially parallel to a skin surface from an extended position to a substantially flush position shown. An outer dimension of the push button 70 is configured to be slidably received in a similar shaped opening in the side of the hub 60. In the exemplary embodiment shown, the hub 60 has a non-circular shape, but is not limited thereto. The shape of the device can be configured in any number of shapes to hold the flexible needle while it is in the device. In other exemplary embodiments of the present invention, a circular hub can be provided to coil the flexible needle therein before use.

The hub 60 further comprises a curved needle or catheter path 68 such that the movement of the push button 70 substantially parallel to a skin surface from an extended position to a substantially flush position, can be used to insert the flexible needle or catheter 80. The flexible catheter 80 is configured to flex and be guided along the curved catheter path 68 from a position substantially parallel to a skin surface to a position substantially perpendicular to a skin surface for insertion at a site as directed by the push button 70. The hub 60 further comprises a tube connection port 62 to which an exemplary tube 64 can be connected to connect the infusion set with a medicament pump or other supply vessel. An adhesive liner 74 can be provided to cover an adhesive layer 76, such as a pressure sensitive adhesive (PSA), on the bottom of the device 10.

The push button 70 comprises at least one projection 72 on a surface to slidably engage a similar opening 64 in the hub 60. The push button 70 is configured to press a septum 66 and flexible catheter 80, such that the flexible catheter 80 is pushed along the curved catheter path 68 toward an insertion site when pressed by a user. An exemplary flexible stainless-steel, in-dwelling, needle or catheter 80 is shown in FIG. 9. As noted, the in-dwelling cannula 80 used in this embodiment is a flexible, skin-piercing needle or catheter that does not require a separate introducer needle.

In the embodiment of FIG. 9, the body of the flexible catheter 80 comprises one or more features to create substantially flexible body segment(s). In one embodiment, an entire length of the catheter can be flexible, but embodiments are not limited thereto. In one exemplary embodiment, the one or more features to create the substantially flexible body segment(s) comprise a slotted structure which allows the shaft to be flexible, maintain column strength, but allow insertion when for example, guided through a curved path. In another exemplary embodiment, the one or more features to create the substantially flexible body segment(s) comprise a series of hoops or coils, wherein the strength of the catheter 80 is maintained and prevents collapse of the inner lumen. The slots, hoops, coils or other features, can be laser cut, chemically etched or otherwise created, in an alternating or other pattern, and the body or portions thereof can then be covered with a sleeve. Exemplary flexible catheters are described in co-pending U.S. patent application Ser. Nos. 13/138,128, 12/585,061, and 12/585,062, the entire contents of which are incorporated herein by reference.

In the exemplary embodiment shown, the alternating slots or coils surround a lumen and enable the needle or catheter 80 to flex to provide a comfortable in-dwelling catheter, but also provide a rigidity or column strength necessary for insertion into the user's skin. The exemplary flexible needle or catheter 80 is preferably a unitary body 82 of a material such as stainless steel, having a sharpened, self-piercing tip 84 at the distal end. The sharpened, self-piercing tip 84 can comprise a radius cut to create a beveled tip. Where the catheter 80 is provided with such a sharpened, self-piercing tip 84 to allow the insertion, the catheter can act as an introducer needle, thereby further reducing the complexity of the insertion step.

Further, the catheter 80 can be sheathed or coated over some desired portion by a coating 86, such as a Vialon™ coating or a Teflon™ coating, to create a sleeve that provides a biocompatible outer fluid seal for enabling a drug fluid to enter to the user through the tip of the catheter 80, provides a seal so that leakage does not occur through the slots, and/or provides a cover into which the self-piercing tip 84 can be slightly retracted to cover the sharpened end thereof. Depending on the specific sheath or sleeve material, the attachment of the sheath or coating can be facilitated by a dip coating process, heat shrinking, bonding, or any other suitable process. In yet other exemplary embodiments of the present invention, any suitable fluid tight material could be used to form the sheath or coating, such as a flexible sleeve or over-molded coating/sleeve. In this or other exemplary embodiments of the present invention, a material which can become softer and/or more flexible once inserted can advantageously be used.

Figure 10:
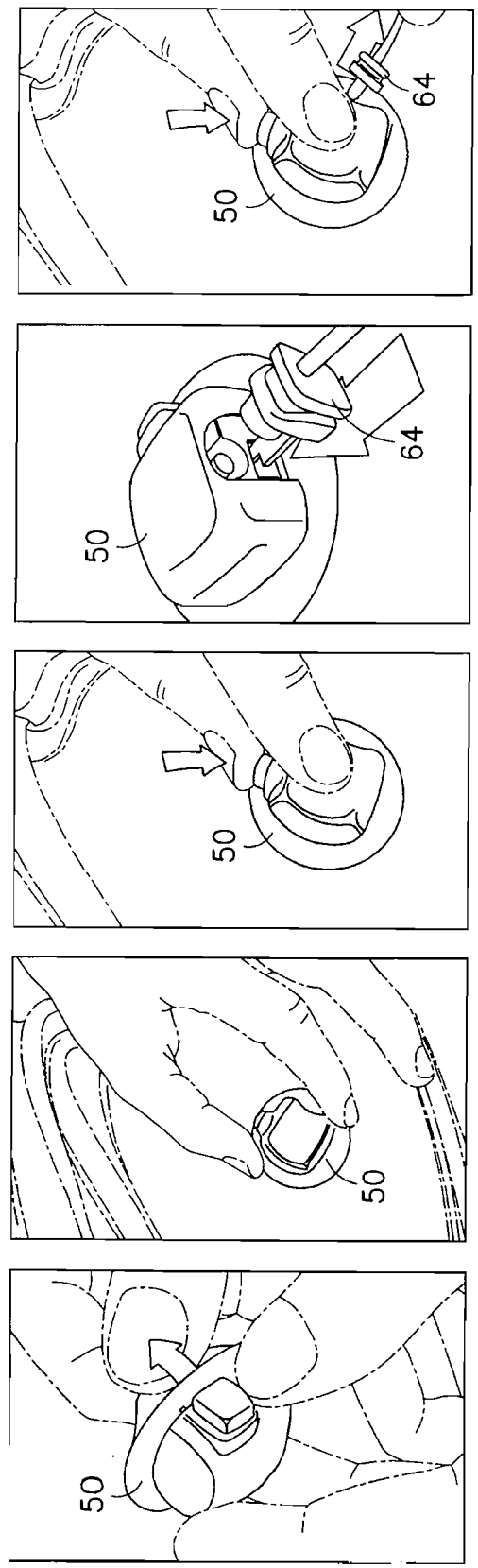
FIGS. 10A-10E are views of the exemplary device of FIG. 6 in use.

FIGS. 10A-10E are views of the exemplary device 50 of FIG. 6 in use. In a first step of FIG. 10A, a user removes the adhesive liner 74 from the lower surface to expose the adhesive layer 76 of the bottom of the device 50. In this position, the flexible catheter 80 is retracted into the hub 60 and the push button 70 is in an extended position. The hub 60 of the device 50 can then be secured to an infusion site using the exposed adhesive layer 76 as shown in FIG. 10B. This ensures that the hub 60 of the device 50 is fully contacting and adhesively secured to the skin surface before the user performs the deployment of the catheter 80. The user can then press the button 70 of the device 50 to insert the catheter 80 in a single motion as shown in FIG. 10C. The tube 64 can then be connected to a pump or other medicament supply.

In an exemplary embodiment of the present invention, the push button 70 can be configured to secure the tube 64 to the device, such that pressing the button 70 permits removal of the tube 64 as shown in FIG. 10E. In an exemplary embodiment, the push button 70 and projection 72 can engage one or more detents (not shown) of the tube 64 connector such that the tube connector and tube 64 cannot be removed from the connection port 62 if the button 70 is in a first position, and can be removed when the button 70 is in a second position.

In the second exemplary embodiment of the present invention, the user can attach the complete device to the skin surface and then deploy the in-dwelling catheter of the infusion set preventing any bunching of the adhesive when attached as well as ensuring that the set hub is fully contacting and adhesively secured to the skin before the in-dwelling catheter is inserted. This also ensures that the in-dwelling catheter is inserted at the correct depth. The exemplary device further provides a flexible steel in-dwelling catheter that can prevent kinking, since it is much stiffer than a conventional Teflon catheter. The device uses a manual method of deployment as the user is required to push the side of the device, such as a button disposed at the side of the device, to insert the in-dwelling catheter.

As noted above, in a conventional system, an introducer needle, catheter, and adhesive, are all deployed at substantially the same time. During such ballistic insertion, there is a high-speed contact of the adhesive pad while the introducer needle and the catheter are being inserted which may result in partially inserted catheters and/or incomplete adhesion. The exemplary second embodiment of the present invention eliminates the potential of partial insertion of the catheter and/or incomplete adhesion, since the system and method first ensures that the hub of the set is fully contacting and adhesively secured to the skin surface and then performs the deployment of the catheter with full control as the user pushes the catheter into the skin using a manual push button operation. The stronger, more flexible catheter completely prevents kinking as it is much stiffer than a conventional Teflon™ catheter.

In doing so, the exemplary second embodiment of the present invention significantly reduces the steps required to insert the infusion set since the user is again not required to load the infusion set into the inserter device. Further, the flexible catheter including sharpened tip is hidden from the user prior to use and insertion, which makes the device more safe and appealing to users who are uncomfortable with needles.

As noted above, the device is configured for the user to attach the device to the skin surface in a first step, then deploy the flexible catheter in a second step, thereby preventing any bunching of the adhesive when attached as well as ensuring that the set hub is fully contacting and adhesively secured to the skin before the flexible catheter is inserted. This also ensures that the catheter is inserted at the correct depth. The provision of a stronger, more flexible catheter substantially eliminates kinking, as it is much stiffer than a Teflon catheter.

In a third exemplary embodiment of the present invention, the device comprises another infusion set and insertion device integrated into a single unit, thereby again eliminating the need to carry any additional accessories and avoid the difficulty associated with loading the infusion set onto the insertion device at each use.

Figure 11:
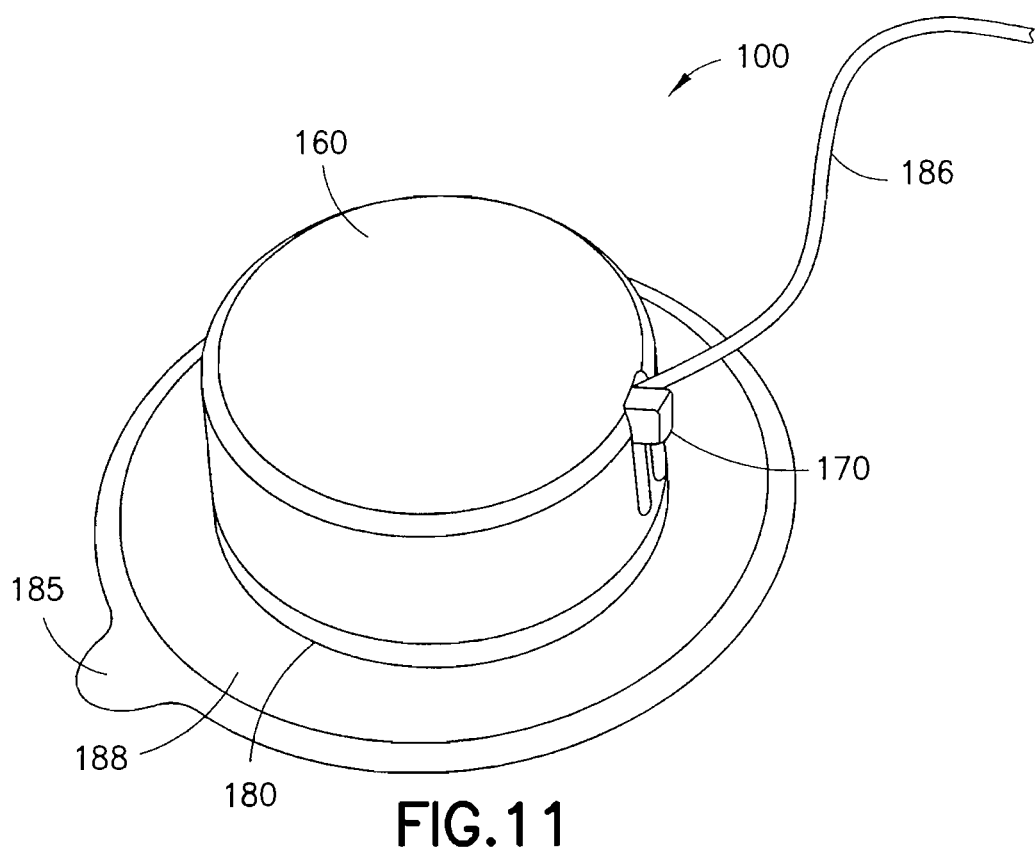
FIGS. 11 and 12 are perspective views of an exemplary device utilizing an integrated inserter and set in accordance with a third embodiment of the present invention before deployment.
Figure 12:
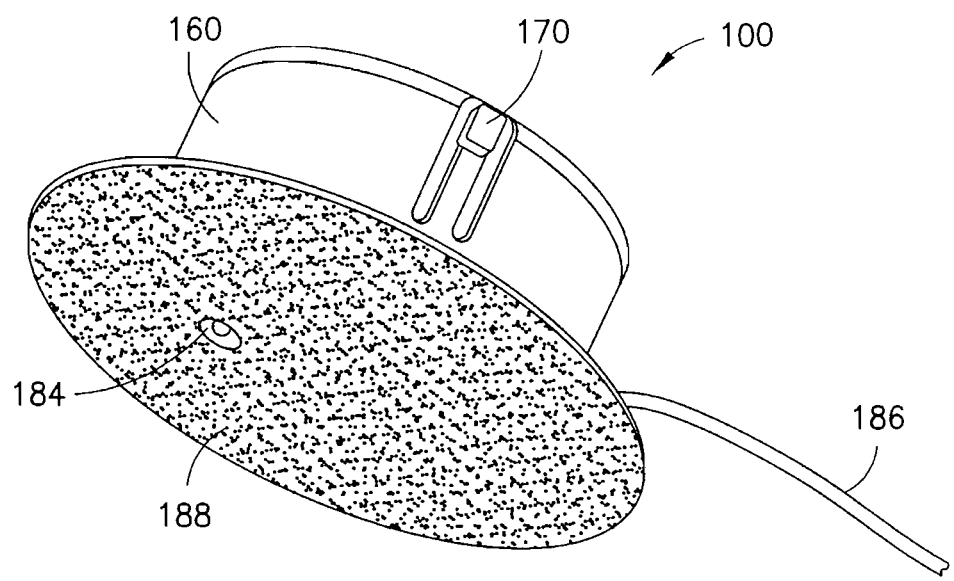
Figure 13:
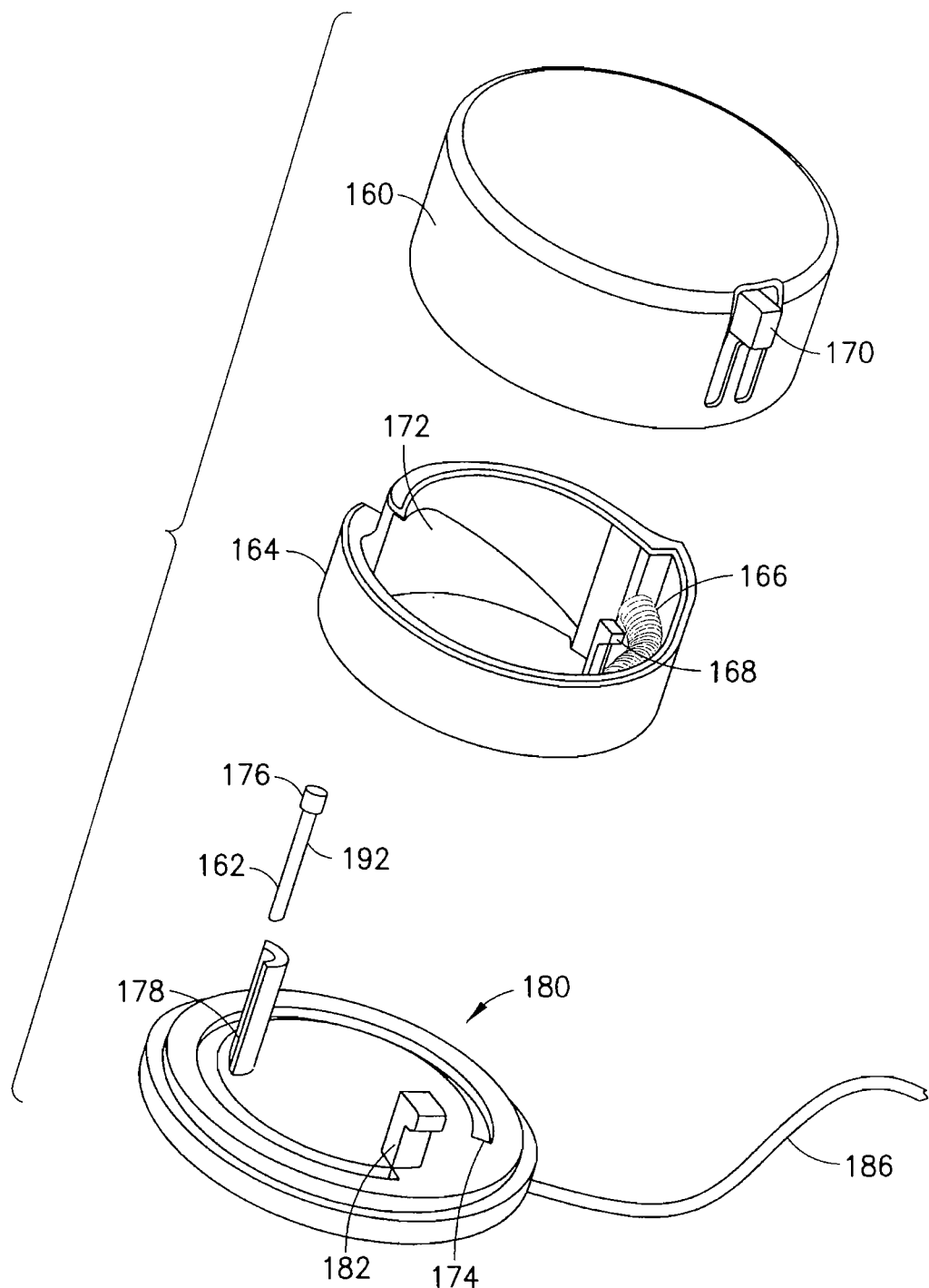
FIG. 13 is an exploded view of the exemplary device of FIG. 11, illustrating the components thereof in greater detail.
Figure 14:
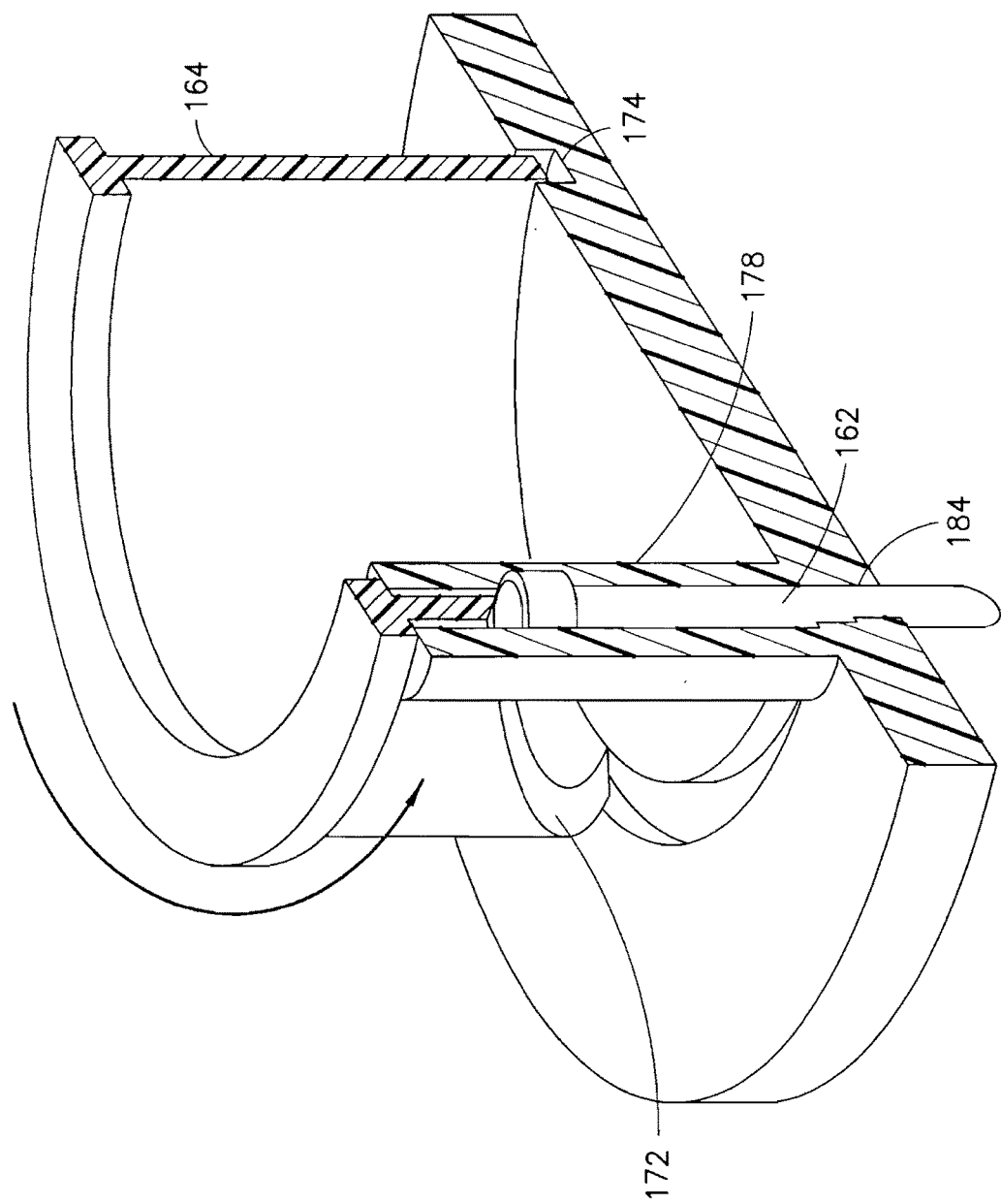
FIG. 14 is an enlarged view illustrating an operation of the exemplary device of FIG. 11.

FIGS. 11 and 12 are views of an exemplary device 100 utilizing an integrated inserter and set in accordance with a third embodiment of the present invention. The device 100 comprises an upper housing 160, from which a user release trigger 170 extends. The upper housing 160 is secured to a lower housing 180, and an in-dwelling cannula 162 can be extended from a bottom surface of the lower housing 180 during activation of the device. FIG. 13 is an exploded view of the exemplary device of FIGS. 11 and 12, illustrating the components thereof in greater detail. FIG. 14 is a view of the feature movements occurring during placement of the in-dwelling cannula 162.

As shown in FIG. 13, the upper housing 160 comprises an opening at a side surface and in which the user release trigger 170 is disposed. The user release trigger 170 is provided as a cantilevered portion of the upper housing 160, secured at one end and free at an opposite end, and having a raised portion at the free end for user engagement. The user release trigger 170 is configured to deflect a spring retainer 168 and release a driving coil spring 166 contained in the upper housing 160.

Specifically, the upper housing 160 contains therein a rotatable cam ring 164, spring 166, spring retainer 168 and cam surface 172. The rotatable cam ring 164 is configured to rotate relative to the upper housing 160 as urged by the spring 166 once released by the spring retainer 168. The lower housing 180 is formed with a cam ring guide 174 to rotatably guide a lower edge of the cam ring 164. A reciprocal guide can be formed in the surface of the upper housing 160 to guide a top edge of the cam ring 164. When released by the user release trigger 170, the spring 166 is configured to rotate the cam ring 164, relative to the upper and lower housings, within the cam ring guide 174. In doing so, an inclined cam surface 172 of the rotating cam ring 164 engages a cannula head 176 of a cannula 162. The cannula 162 is prevented from rotating with the cam ring 164 by placement of the cannula 162 in a C-shaped guide feature 178 extending perpendicular to a surface of the lower housing 180.

As shown in FIG. 14, the rotating motion of the cam ring 164 is translated into a linear motion of the cannula 162 in the guide feature 178 to drive the cannula 162 into placement through a guiding septum 184. The cam ring 164 movement is stopped by a cam stop 182 coinciding with desired cannula 162 placement depth. In the exemplary embodiment shown, the device 100 has a circular shape, but is not limited thereto. The shape of the device can be configured in any number of shapes, but having a circular portion to permit cam ring rotation.

A line or extension set 186 can then be attached to the upper or lower housing, or as shown in FIG. 13, can be manufactured with the lower housing 180, and can be connected to a medicament pump or other supply vessel. An adhesive liner 185 can be provided to cover an adhesive layer 188, such as a pressure sensitive adhesive (PSA), on the bottom of the device.

In doing so, the third exemplary embodiment provides a low-profile assembly that is part of an insulin infusion set. The low-profile assembly incorporates a rigid steel needle that remains in-dwelling and is deployed to a depth of preferably 4.0 mm to 4.5 mm into the surface of the skin, i.e. 1.0 mm to 1.5 mm into subcutaneous tissue. The overall height of the assembly is preferably 3.8 mm higher than the deployment depth (i.e., for subcutaneous deployment to a depth of 4.5 mm, the profile is 8.3 mm, and for intradermal deployment to a depth of 1.5 mm, the profile is 5.3 mm).

In another example, the overall height of the assembly is 6.5 mm, and the necessary mechanization for deployment and structural components of the assembly increase the overall height of the assembly by preferably 2.5 mm beyond the deployment depth. In this case, deploying a steel needle to a depth of preferably 1.5 mm into the surface of the skin, i.e. into intradermal tissue, the overall height of the assembly is preferably 4.0 mm, i.e. 1.5 mm into tissue plus preferably 2.5 mm for mechanization and structural components. In yet other exemplary embodiments, to further reduce the height of the assembly by 1 mm or more, the elements can be thinned and incorporate a splined collar over the introducer needle to advance the needle from the side instead of from above with the cam ring as described above.

In the third exemplary embodiment, the in-dwelling steel cannula 162 is preferably straight with a cross-port 192 to allow insulin to flow from a septum cavity into the cannula. The shouldered head 176 is attached to the top end of the cannula 162 to block flow from the top end and to also provide a contact surface for the cam surface 172 of the cam ring 164 to drive the cannula 162 into the tissue. Slots can be machined into the rigid in-dwelling steel needle in the area of the skin interface, device interface or elsewhere, using laser machining, chemical etching, electrical discharge machining, or other metal removal processes, to render that portion of the rigid cannula flexible, thereby reducing or eliminating the effects of transferring motion through the sharp tip of the cannula to the tissue. To eliminate leak paths through the machined slots into the tissue at the skin, a thin-walled (i.e., 0.0005 inch thick) sleeve of tubing, such as Teflon shrink tubing or another heat shrinkable tubing material, can be shrunk onto the in-dwelling flexible steel needle above and below the slotted area. Exemplary flexible catheters, catheter construction and coatings are described in co-pending U.S. patent application Ser. Nos. 13/138,128, 12/585,061, and 12/585,062, the entire contents of which are incorporated herein by reference.

Figure 15A:
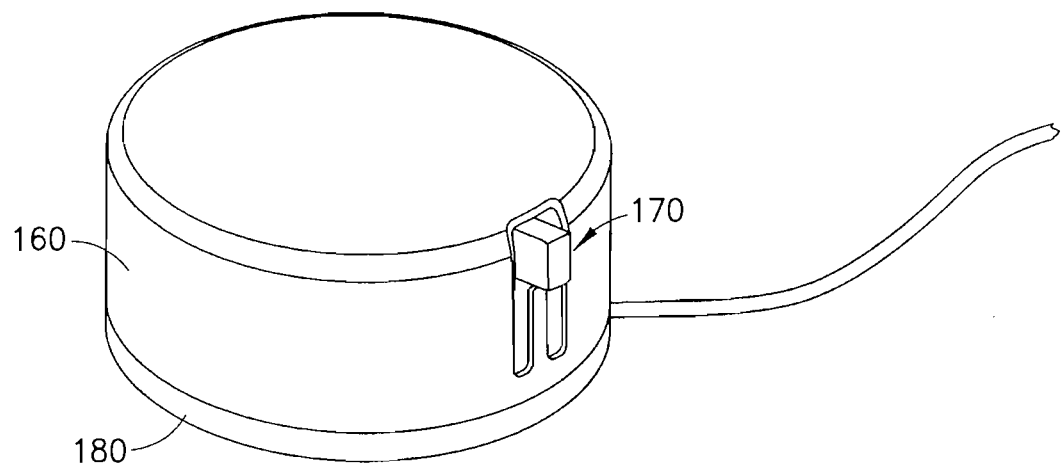
FIGS. 15A-15D are views of the exemplary device of FIG. 11 in use.
Figure 15B:
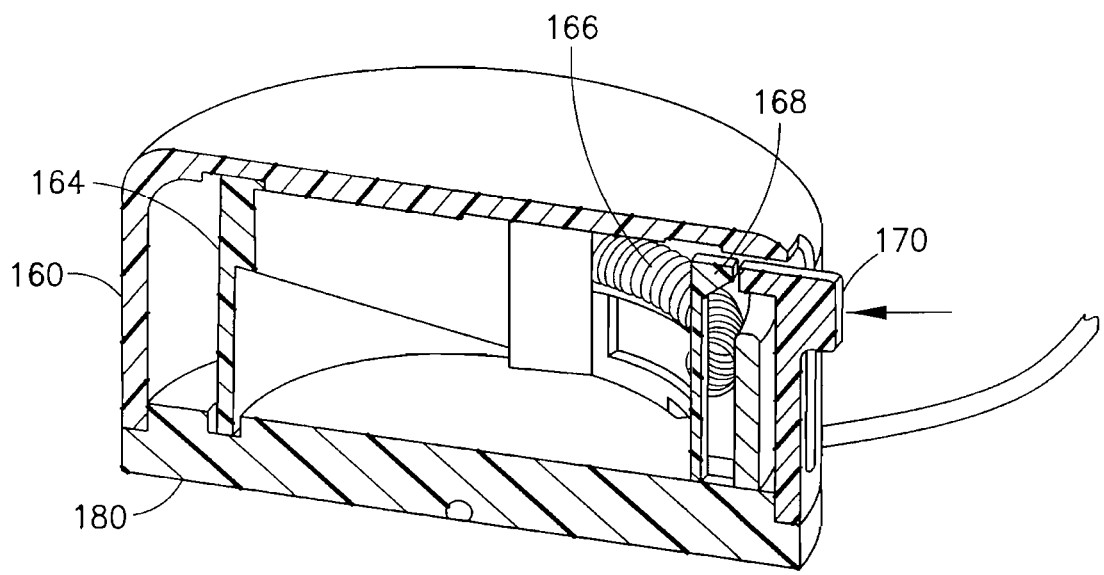
Figure 15C:
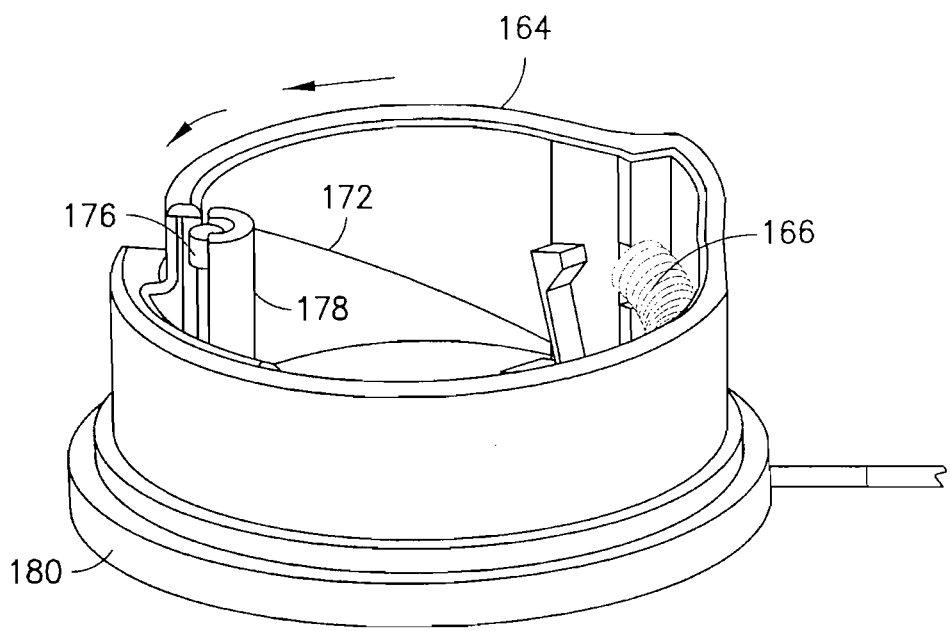
Figure 15D:
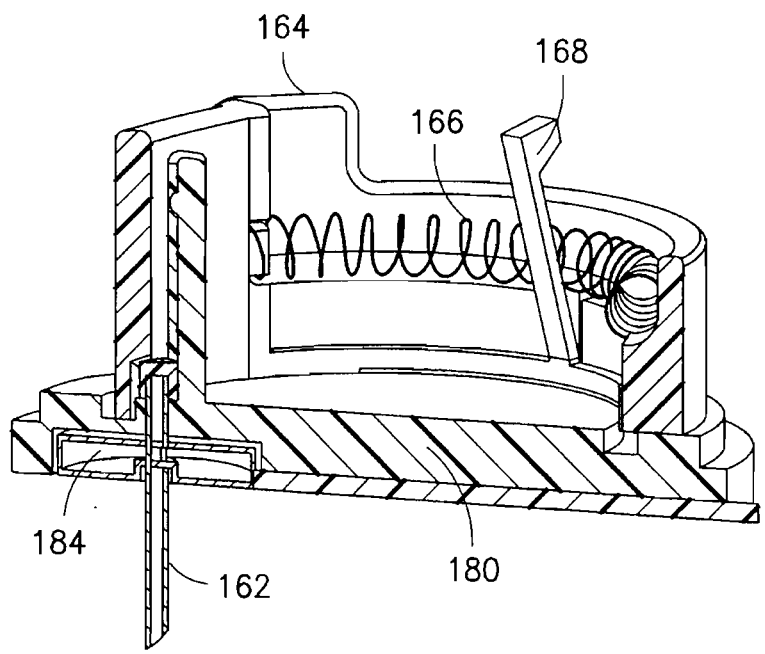

FIGS. 15A-15D are views of the exemplary device 100 of FIG. 11 in use. In a first step of FIG. 15A, a user removes the adhesive liner from the lower surface to expose the adhesive layer 188 of the bottom of the device. In this position, the cannula 162 is retracted into the lower housing 180. The device 100 is then secured to an infusion site using the exposed adhesive layer 188. This ensures that the device 100 is fully contacting and adhesively secured to the skin surface before the user performs the deployment of the cannula 162. The user then presses the user release trigger 170 of the device 100 to release the rotating cam ring 164 to insert the cannula 162 in a single motion as shown in FIGS. 15B and 15C. A final position is shown in FIG. 15D. If not already connected, the tube 186 can then be connected to a pump or other medicament supply.

The third exemplary embodiment can further provide a small footprint, preferably about 14.2 mm in diameter, permitting the use of a strain relief feature, which can extend the use duration of an infusion set. In this case, the complete footprint of device and strain relief feature can be approximately the size of currently available infusion sets. Exemplary strain relief features are described in co-pending U.S. Provisional Patent Application Ser. No. 61/441,278, the entire contents of which are incorporated herein by reference.

Figure 16:
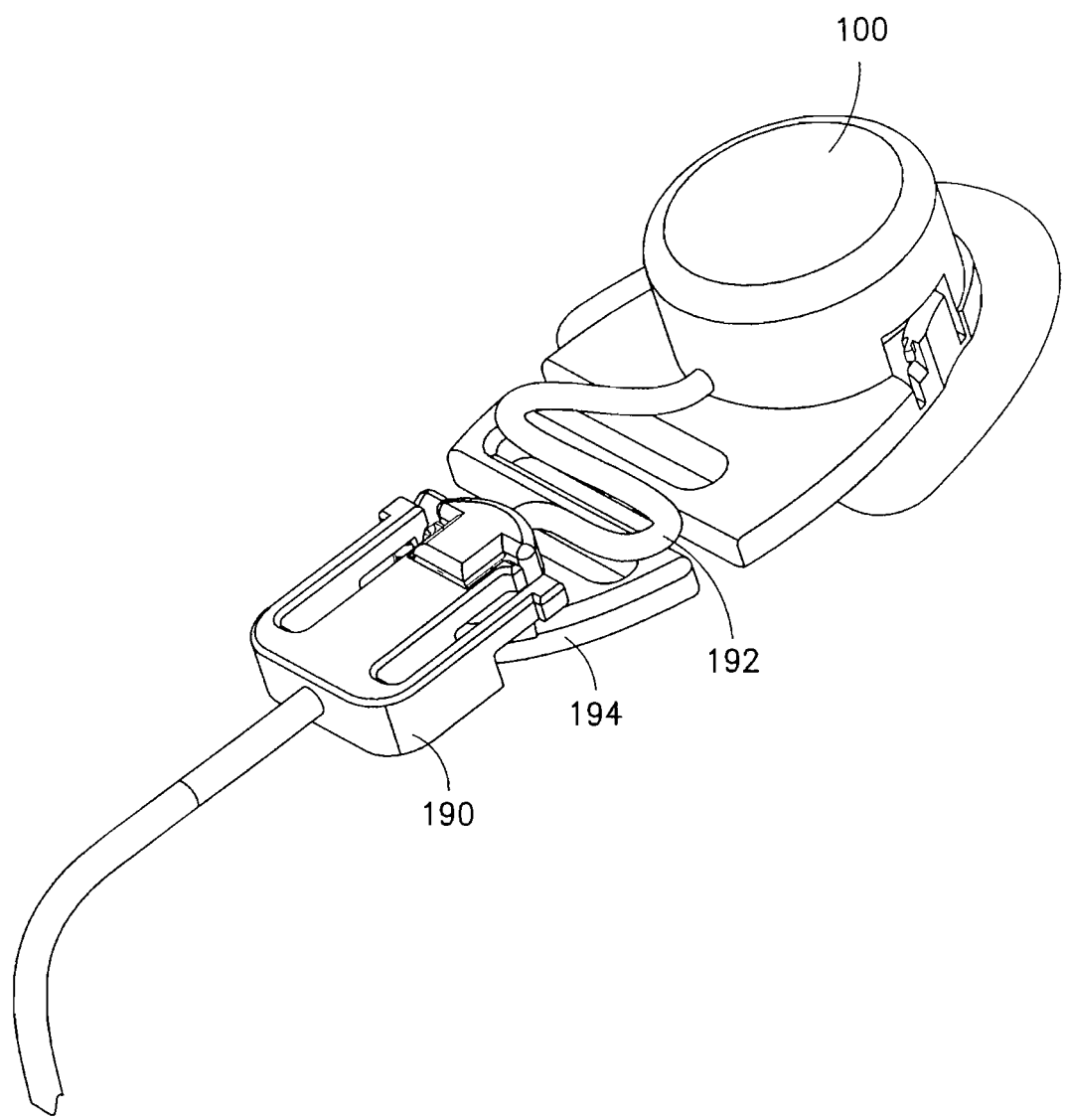
FIG. 16 is a perspective view of a strain relief device that can be provided with the exemplary device of FIG. 11 in use.

FIG. 16 is a perspective view of a strain-relief that can be provided with the exemplary device of FIG. 11 in use. As shown in FIG. 16, the device 100 can be coupled with the line set via an attachment 190 that can comprise an accordion tube connection 192 between the attachment 190 and the device 100. The attachment 190 can further comprise a separate adhesive layer 194 to adhesively secure the attachment to the skin surface. The adhesive layer 194 can be connected to the adhesive layer of the device either directly, or via an accordion shaped adhesive segment matching the tubing section 192. The same adhesive cover can be provided for both layers 188 and 194.

In yet other exemplary embodiments, the cam ring, cam surface, cannula and cannula head can be modified to utilize an introducer needle to deploy a catheter. Similar to the in-dwelling steel needle described above, the introducer needle could be rendered flexible in the area of the device interface or tissue interface to allow the introducer needle to remain in-dwelling. Alternately, the cam ring, cam surface, cannula and cannula head can be modified to allow the introducer needle to be either partially retracted such that the sharp tip of the introducer needle is retracted within the tip of the catheter, or completely retracted such that the introducer needle is retracted within the body of the hub. For all alternative embodiments the overall height of the assembly can be maintained at preferably 2.5 mm greater than the deployment depth.

Figure 17:
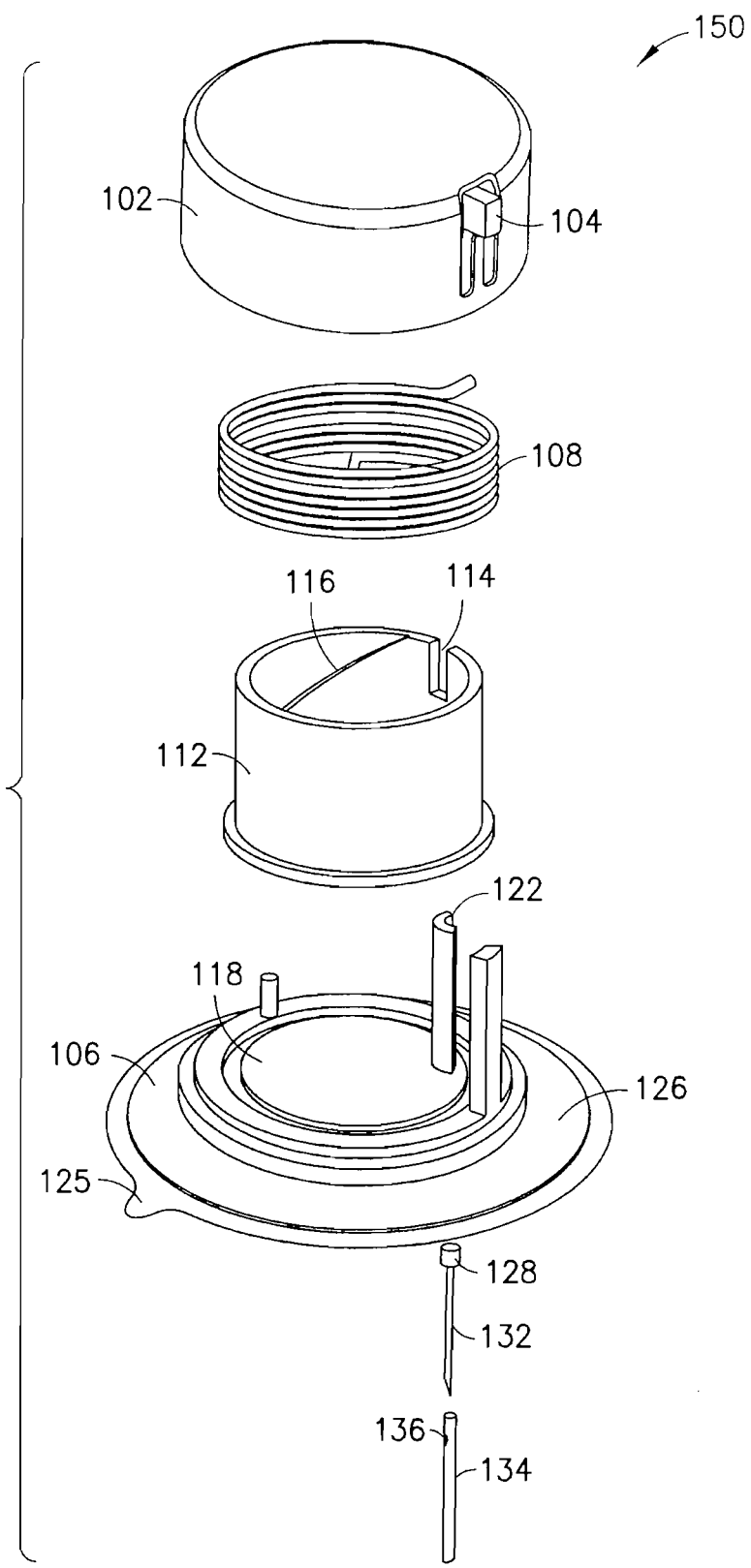
FIG. 17 is an exploded view of the exemplary device of FIG. 11 illustrating alternative spring and cannula types in greater detail.

FIG. 17 is an exploded view of the exemplary device of FIG. 11 illustrating alternative spring and cannula types in greater detail. The device 150 can comprise an upper housing 102, release trigger 104 and lower housing 106 substantially as described in regard to the embodiment above, including an adhesive liner 125 that can be provided to cover an adhesive layer 126, such as a pressure sensitive adhesive (PSA), on the bottom of the device 150. A torsion spring 108 is disposed within the upper housing 102 to surround a rotatable cam ring 112. The torsion spring 108 exhibits different performance characteristics as compared to the coil spring 66 in the embodiment above. As in the embodiment described above, the rotatable cam ring 112 is configured to rotate relative to the upper and lower housings as urged by the torsion spring 108 when released by the trigger 104. Upper and lower spring retainer detents 114 are provided on the cam ring 112 to hold the ends of the torsion spring during operation. In yet other exemplary embodiments, the spring can be eliminated entirely, and replaced with an external driving unit to drive the cam ring. For example, a pre-charged driver can be used to engage the cam ring using, for example, keys on an outer diameter, to rotate the cam ring for desired operation.

The lower housing 106 includes a cam ring guide 118 to rotatably guide the cam ring 112 during operation. A reciprocal guide can be formed in the surface of the upper housing 102 to guide a top edge of the cam ring 112. As described in regard to the embodiment above, the lower housing 106 further includes a C-shaped guide feature 122 to guide in this case, an introducer needle 132 having a cannula head 128 to place a cross-ported catheter 134 through a septum 124 in the lower housing 106. In an exemplary embodiment, the device comprises a 28 gauge catheter, having a cross-port 136 at an upper portion thereof, and a 31 gauge introducer needle, but is not limited thereto.

Figure 18A:
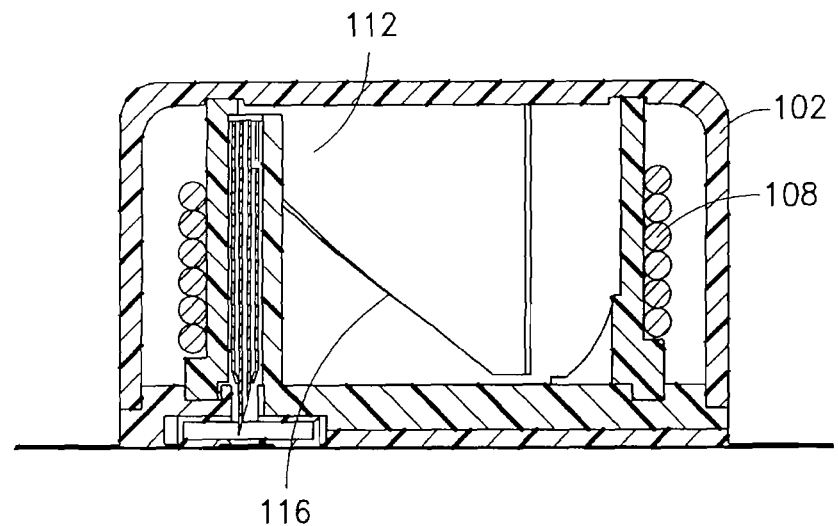
FIGS. 18A and 18B are enlarged views illustrating the operation of the exemplary device of FIG. 17.
Figure 18B:
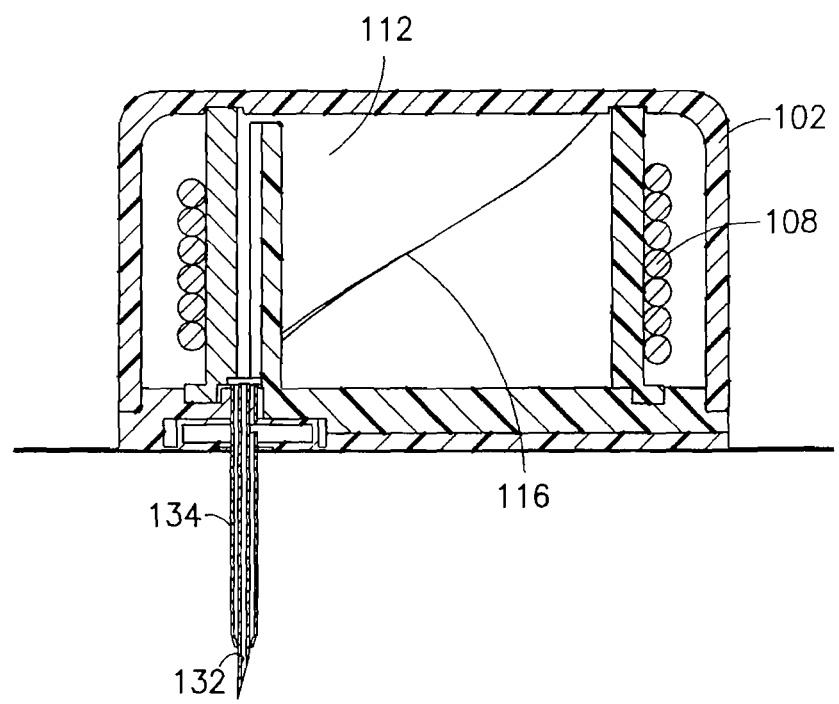

FIGS. 18A and 18B are enlarged views illustrating an operation of the exemplary device of FIG. 17. As shown in FIG. 18A, the release of the torsion spring 108 can be used to rotate the cam ring 112 which can direct movement of the introducer needle 132 and catheter 134 by directing movement of the cannula head 128 using the cam surface 116. The cam surface 116 is configured to move the cannula head 128 to first drive the introducer needle 132 and catheter 134 through the septum 124 in the lower housing 106 and into a skin surface. Further movement of the cam ring 112 and the cam surface 116 is configured to move the cannula head 128 to either partially or fully retract the introducer needle 132 into the lower housing 106.

In the exemplary embodiment of FIG. 17 the overall height of the device can be preferably 8.3 mm as a result of recessing the introducer needle inside the assembly. For example, at an upper portion of the cannula, an upper housing can be provided with a thickness of 0.75 mm, a portion of the cam ring that extends above the cannula head can be 0.4 mm, a cannula head thickness can be 0.4 mm, and a distance for the cannula cross-port to the cannula head can be 0.4 mm. At a portion where the cannula exits the lower housing, a distance from the cross-port to the bottom of the septum can be 0.4 mm, and an adhesive thickness can be 0.1 mm. At a portion where the introducer needle extends form the catheter, a gap from the tip of the introducer needle to the far side of the adhesive can be 0.25 mm, and the tip of the introducer needle can extend 1.1 mm, for a total of 3.8 mm. Further reduction in the overall height can be accomplished by assembling the introducer needle to extend from the adhesive by 1 mm to 2 mm without affecting use. Further, a cam ring having two or more stages can be used to reduce the height and component thickness above the cannula head.

Many hubs and inserters are designed to deploy the introducer needle into tissue with the same motion used to place the adhesive onto the skin. A common misuse failure occurs when deployment is incomplete and the user then wipes or otherwise presses the hub or patch to the skin surface causing either the catheter to kink, the depth of deployment to be shallow, or both. The third exemplary embodiment prevents such misuse failures by providing the adhesive which secures the device to the surface of the skin, and then providing the deployment of the cannula by a separate motion and mechanization.

Further, such integrated inserters typically add significant height and volume to the assembly. The assembly of the third embodiment is smaller than most currently marketed assemblies which do not incorporate an inserter. Lower height relates to less physical interference with obstacles potentially resulting in less transfer of motion and improved comfort for the patient. The reduced footprint also equates to improved comfort.

Also, integrated inserters typically increase the complexity of the mechanization in the assembly, making the devices prone to failure and user error. In the third embodiment, only two extra components are added to provide the integrated insertion function. Either a bottom up or top down assembly process (i.e., an assembly sequence in which the components can be stacked from either the lower or upper housing) can be used. A single production line can be utilized, and use carryover components with less development time for each.

This embodiment provides the ability to use a rigid in-dwelling needle for subcutaneous infusion, a flexible in-dwelling needle with heat shrinkable sleeve for subcutaneous infusion, a rigid in-dwelling needle for intradermal infusion, and a flexible in-dwelling needle with heat shrinkable sleeve for intradermal infusion. A catheter with flexible introducer needle, both fully deployed, can be provided. Also, the cam ring, cam surface, cannula and cannula head can be modified to retract such an introducer needle either partially or completely to reduce or eliminate the effects of motion on the tissue at the infusion site. Any in-dwelling steel needle and introducer can also be rendered flexible to reduce or eliminate the effects of motion on the tissue at the infusion site. Accordingly, the third embodiment provides the desired functions while having a lower profile, smaller footprint, less complexity, and lower cost than assemblies of competitive products.

In a fourth exemplary embodiment of the present invention, the device comprises another infusion set and insertion device integrated into a single unit, thereby again eliminating the need to carry any additional accessories and avoid the difficulty associated with loading the infusion set onto the insertion device at each use.

Figure 19:
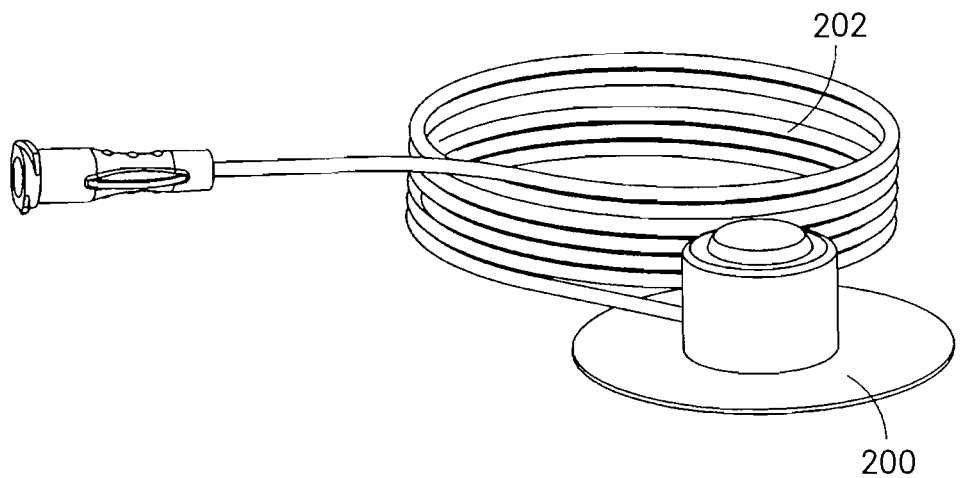
FIG. 19 is a perspective view of an exemplary device utilizing an integrated inserter and set in accordance with a fourth embodiment of the present invention before deployment.
Figure 20:
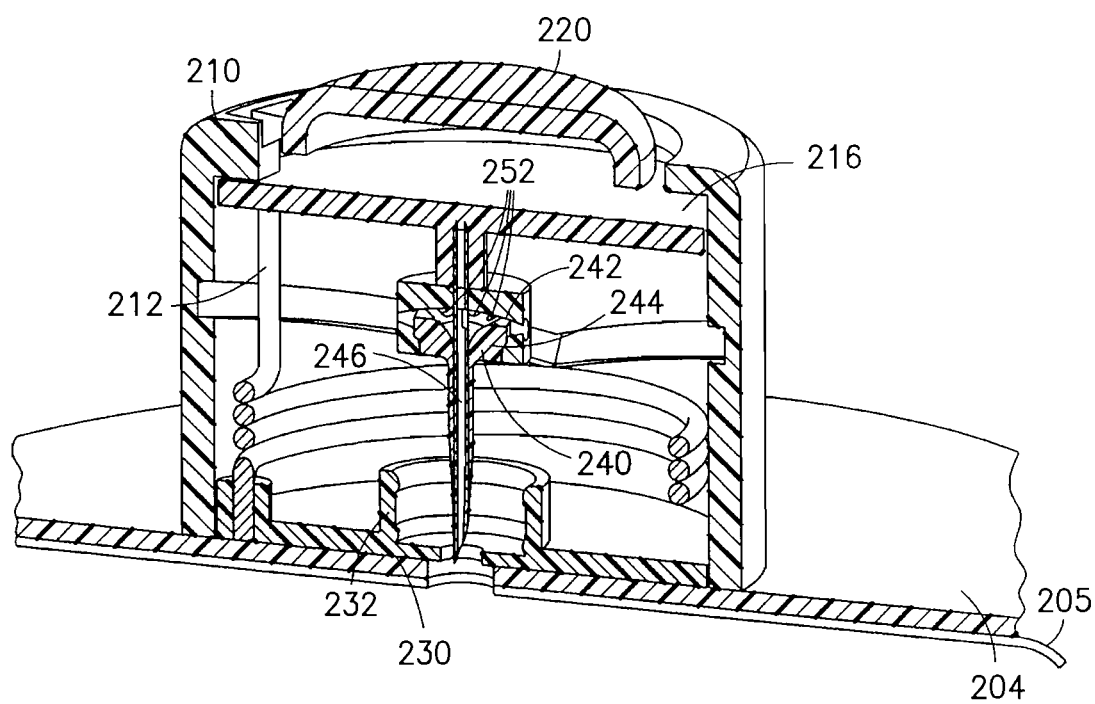
FIG. 20 is a cross-sectional view of the exemplary device of FIG. 19, illustrating the components thereof in greater detail.

FIG. 19 is a view of an exemplary device 200 utilizing an integrated inserter and set in accordance with a fourth embodiment of the present invention and FIG. 20 shows the components therein in greater detail. The device 200 comprises an upper housing 210, from which a button 220 extends. The upper housing 210 is secured to a base 230. Within the upper housing 210, a catheter assembly 240 having a catheter septum 242, catheter 244 and introducer needle 246 are held in an up and retracted position by the contact friction of the introducer needle 246 within the catheter 244. The base 230 can further provide an opening 232 that surrounds a travel path of the catheter septum 242 to thereby guide the catheter septum 242 during insertion of the catheter 244 and introducer needle 246. The opening 232 can further provide seals 234 to seal perforations of the catheter septum 242, and at least one fluid channel 236 as described in greater detail below.

Figure 21:
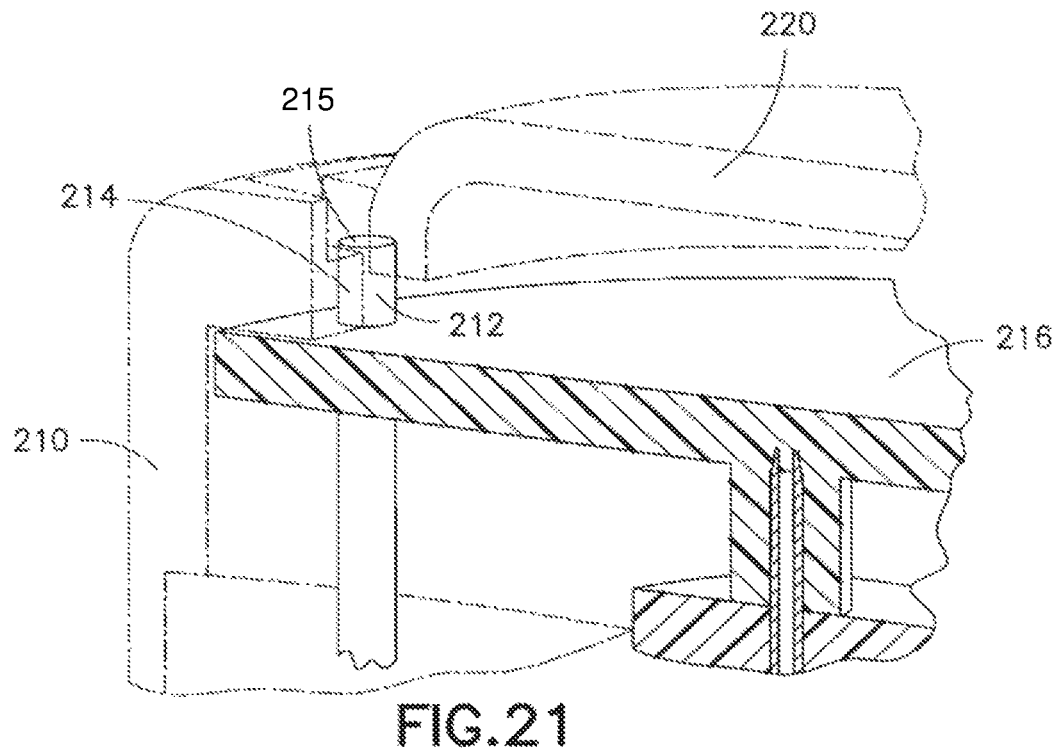
FIG. 21 is an enlarged view illustrating a button operation of the exemplary device of FIG. 19.

As shown in FIG. 21, the upper housing 210 comprises an opening at a side surface and in which an end of a torsion spring 212 engages an upper housing sear 214 to prevent rotation of the torsion spring 212. The button 22 comprises an activation surface 215 to press the end of the torsion spring 212 free of the sear 214 to permit rotation of the torsion spring 212. The upper housing 210 further comprises a rotary needle hub 216 through which the end of the torsion spring extends and which is configured to rotate relative to the upper housing 210 when the end of the torsion spring 212 is pushed free of the sear 214 to permit rotation of the torsion spring 212.

Figure 22:
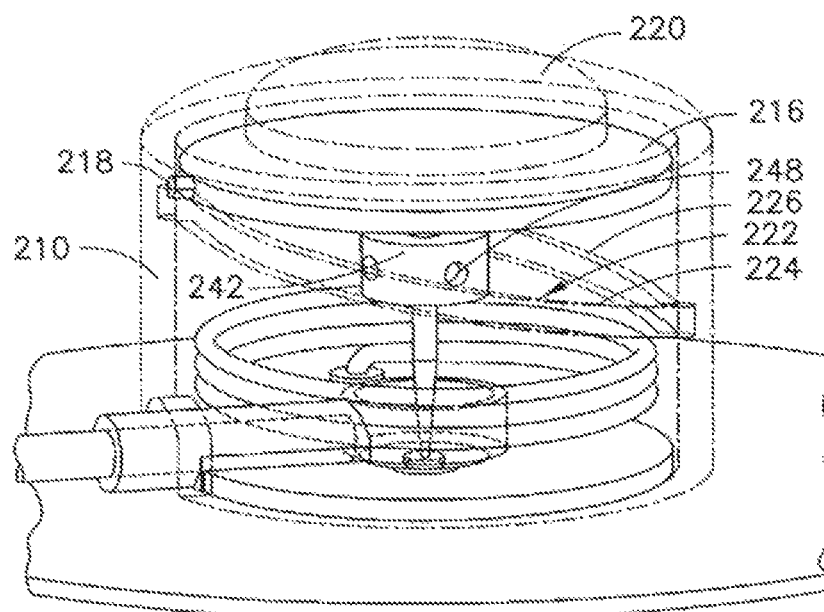
FIGS. 22-24 are views of the exemplary device of FIG. 19 in use illustrating a travel path established by the cam track during use.
Figure 23:
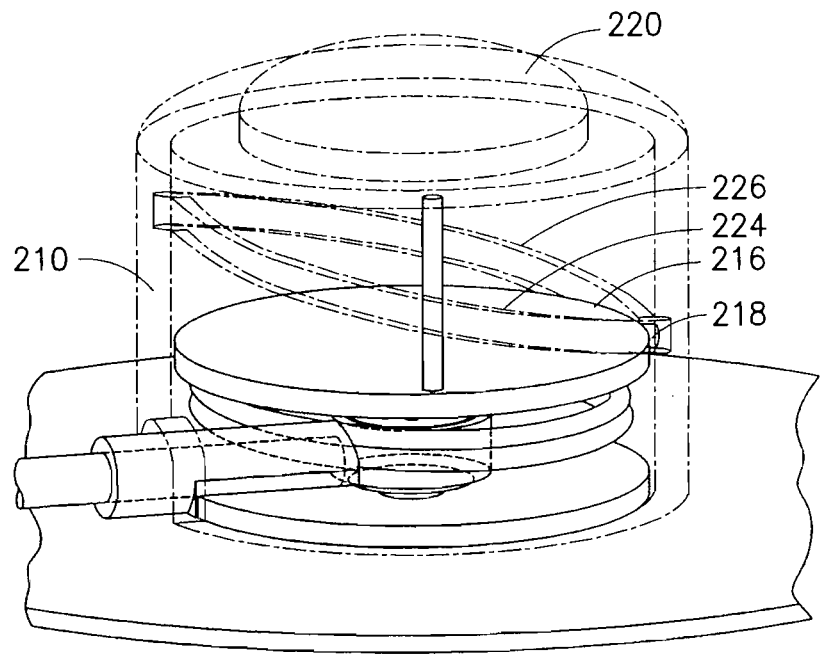
Figure 24:
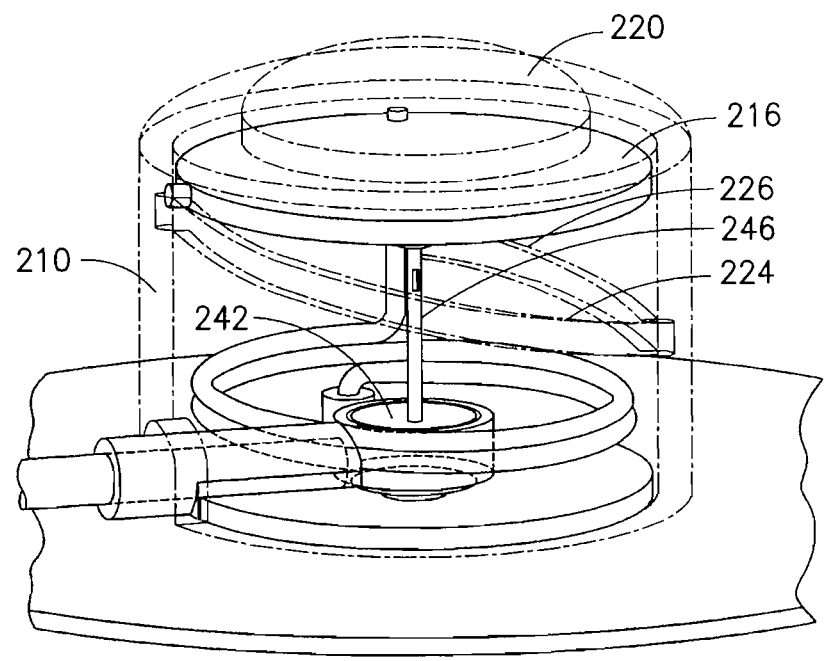

Specifically, the rotary needle hub 216 comprises a rotary needle hub follower pin 218 which is configured to travel within a track 222 on an inner surface of the upper housing 210. The track 222 has two sections. An insertion track profile 224 is provided to move the rotary needle hub 216 including catheter septum 242, catheter 244 and introducer needle 246 toward the skin surface, and a retraction track profile 226 is provided to move the rotary needle hub 216 and introducer needle 246 away from the skin surface, leaving the catheter septum 242 and catheter 244 in the down position. As shown in FIGS. 22-24, the rotating motion of the rotary needle hub 216 is translated into a linear motion of the catheter septum 242, catheter 244 and introducer needle 246 to drive the catheter 244 and introducer needle 246 into placement. In the exemplary embodiment shown, the device 200 has a circular shape, but is not limited thereto. The shape of the device can be configured in any number of shapes, but having a circular portion to permit cam ring rotation.

A line set 202 can then be attached to the upper housing 210, or as shown in FIG. 19, can be manufactured with the upper housing 210, and can be connected to a medicament pump or other supply vessel. An adhesive liner 205 can be provided to cover an adhesive layer 204, such as a pressure sensitive adhesive (PSA), on the bottom of the device.

Figure 27:
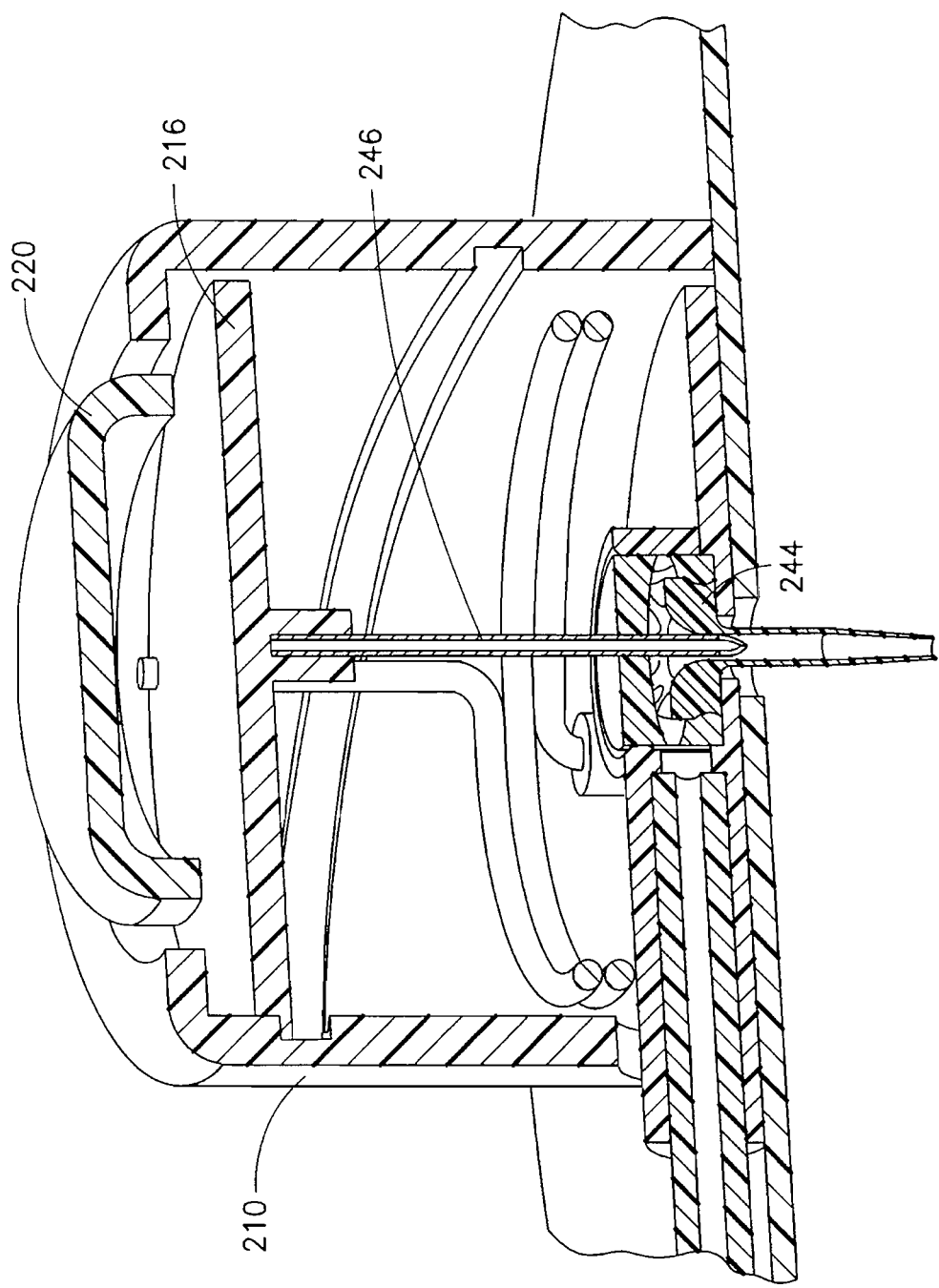

In the exemplary fourth embodiment, the rotary needle hub follower 218 is engaged in the cam track 222. When the torsion spring 212 is released from the upper housing sear 214, the spring imparts a torque on the rotary needle hub 216 causing it to rotate. The rotary needle hub follower 218, secured to the rotary needle hub 216, initially follows the cam track needle insertion profile 224, moving the catheter septum 242, catheter 244 and introducer needle 246 downward, penetrating the patient's skin as depicted in FIGS. 22 and 23. As the rotary needle hub 216 continues to turn, the rotary needle hub follower 218 enters the cam track needle retraction profile 226, withdrawing the rotary needle hub 216 and the introducer needle 246 from the patient's skin, as shown in FIGS. 24 and 27. The catheter septum 242 and catheter 244 remain in the base 230, either by the frictional force imparted by the seals 234 of opening 232 or by some other means of latching. The introducer needle 246 can be fully or partially withdrawn, depending on the shape of the track 222 profile.

Figure 25:
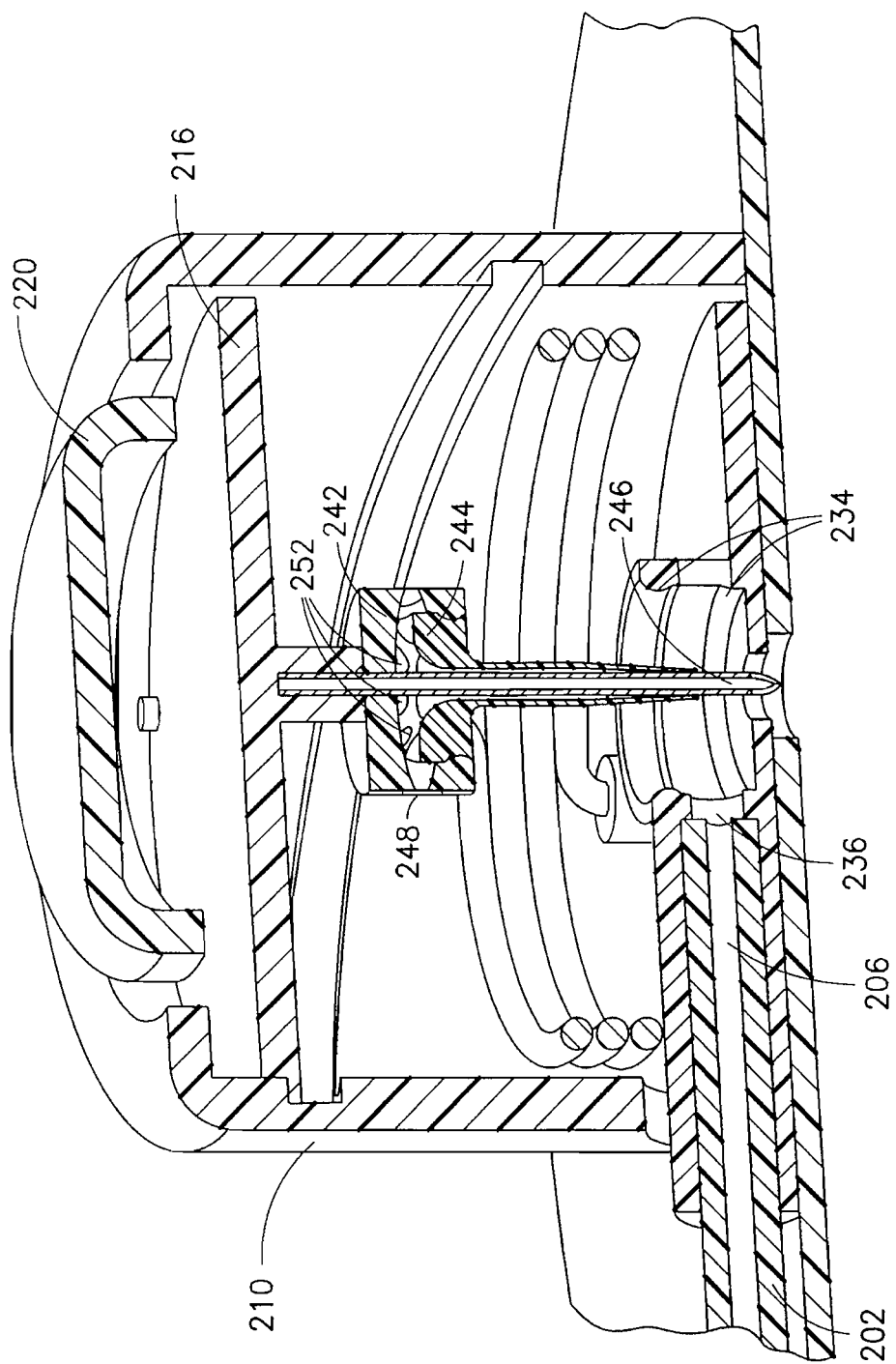
FIGS. 25-27 are views of the exemplary device of FIG. 19 in use illustrating a travel path of the needle hub during use.
Figure 26:
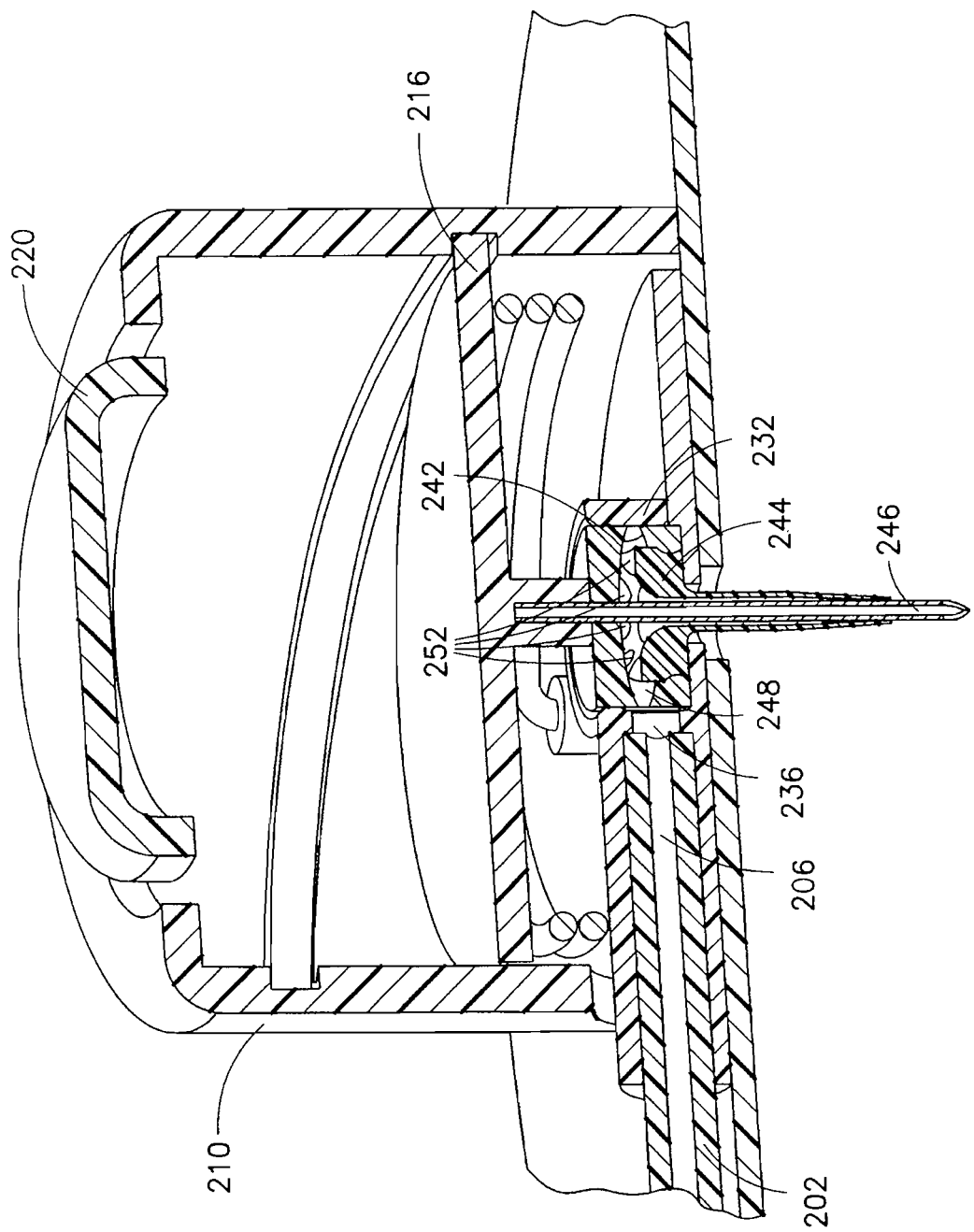

In the fourth exemplary embodiment, a fluid path is created as shown in FIGS. 25-27. Specifically, the catheter septum 242 comprises a number of septum perforations 248 as shown in FIG. 22. When the catheter septum 242 is positioned in the opening 232 of the base 230, the perforations 248 of the catheter septum 242 are sealed above and below the channel 236 by the seals 234. Fluid enters the base 230 via the lumen 206 of the tube set 202, passes through the channel 236 and into a cavity created by the seals 234 and outer body of the septum, then through the septum via the septum perforations 248, and enters the catheter 244 via the catheter perforations 252.

In an exemplary use, a user removes the adhesive liner from the lower surface to expose the adhesive layer 204 of the bottom of the device. In this position, the rotary needle hub 216, catheter septum 242, catheter 244 and introducer needle 246 are retracted into the upper housing 210 and the button 220 is in an extended position. The device 200 can then be secured to an infusion site using the exposed adhesive layer 204. This ensures that the device 200 is fully contacting and adhesively secured to the skin surface before the user performs the deployment of the rotary needle hub 216, catheter septum 242, catheter 244 and introducer needle 246. The user can then press the button 220 of the device 200 to release the torsion spring 212 from the upper housing sear 214 and drive the rotary needle hub 216, catheter septum 242, catheter 244 and introducer needle 246 into position. The continued torsion spring 212 movement drives the rotary needle hub 216 and introducer needle 246 into a retracted position If not already connected, the tube 202 can then be connected to a pump or other medicament supply.

In a fifth exemplary embodiment of the present invention, the device comprises another infusion set and insertion device integrated into a single unit, thereby again eliminating the need to carry any additional accessories and avoid the difficulty associated with loading the infusion set onto the insertion device at each use.

Figure 28:
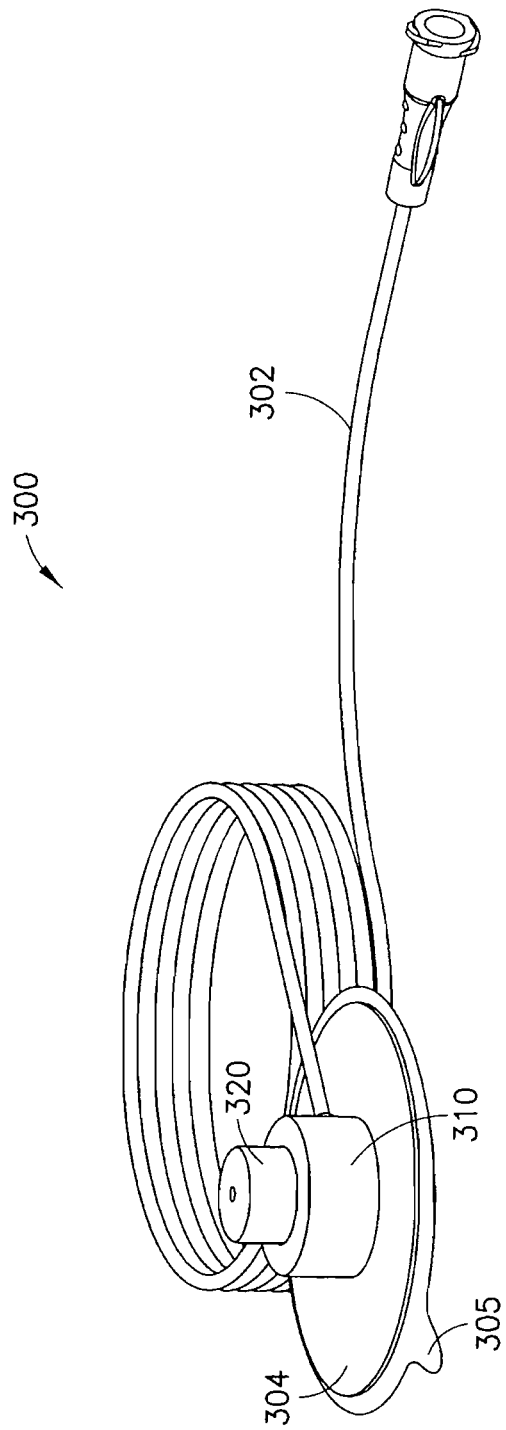
FIG. 28 is a perspective view of an exemplary device utilizing an integrated inserter and set in accordance with a fifth embodiment of the present invention before deployment.
Figure 29:
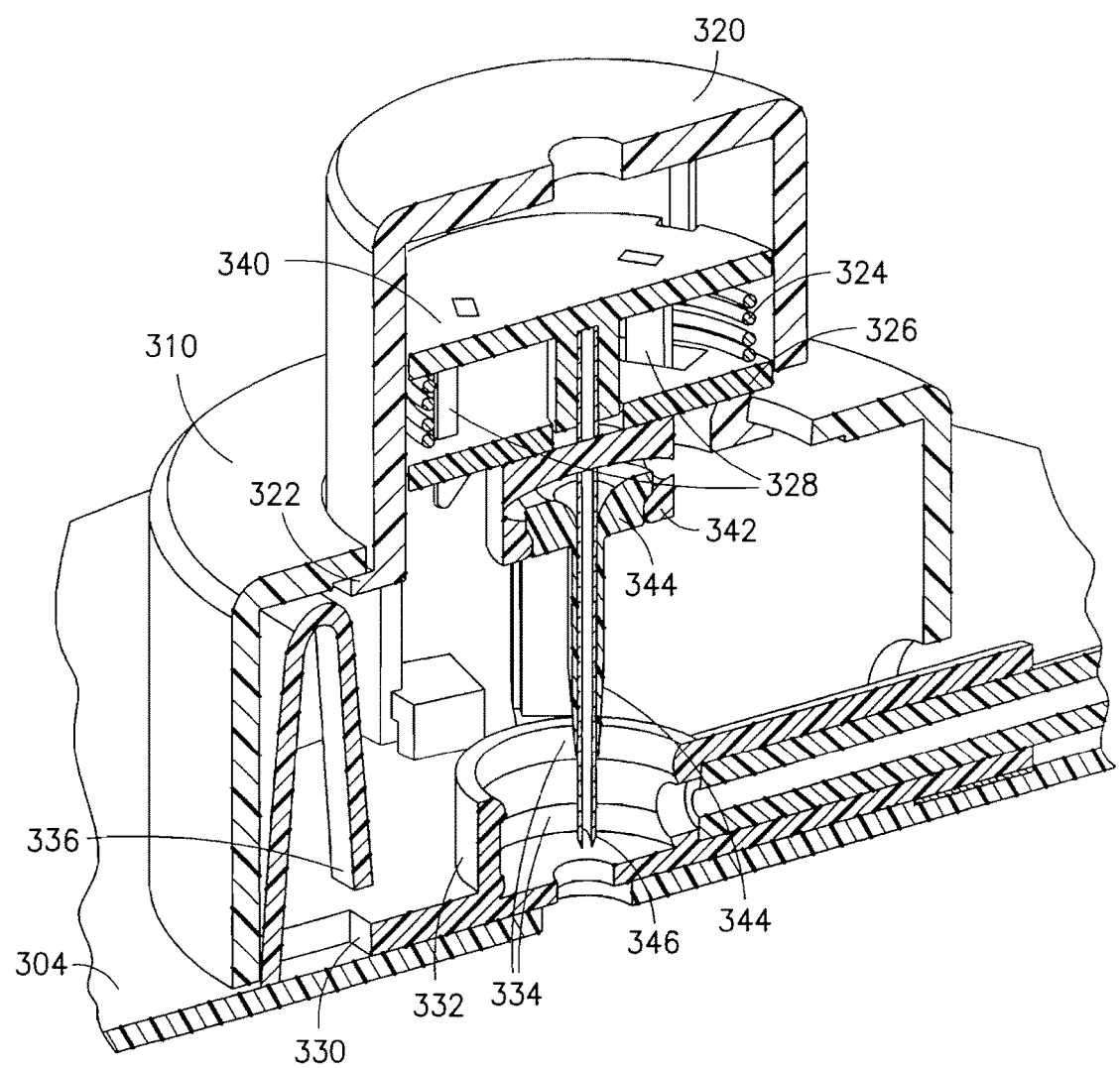
FIG. 29 is an enlarged cross-sectional view of the exemplary device of FIG. 28, illustrating the components thereof in greater detail prior to activation.

FIG. 28 is a view of an exemplary device 300 utilizing an integrated inserter and set in accordance with a fifth embodiment of the present invention and FIG. 29 shows the components therein in greater detail. The device 300 comprises an upper housing 310, from which a button 320 extends. The upper housing 310 is secured to a base 330. Within the upper housing 310 and button 320, a needle hub assembly 340 having a catheter septum 342, catheter 344 and introducer needle 346 are held in an up and retracted position by the contact friction of the introducer needle 346 within the catheter 344. The catheter septum 342, catheter 344 and introducer needle 346 are substantially the same as described in regard to the fourth embodiment above.

The base 330 can further provide an opening 332 that surrounds a travel path of the catheter septum 342 to thereby guide the catheter septum 342 during insertion of the catheter 344 and introducer needle 346. The opening 332 can further provide seals 334 to seal perforations of the catheter septum 342, and at least one fluid channel 336 as described in greater detail below. The opening 332, seals 334 and fluid channel 336 are substantially the same as described in regard to the fourth embodiment above.

The upper housing 210 comprises an opening in a top surface to slidably receive the push button 320, which is captured within the upper housing by shoulders 322. The needle hub 340 is slidably disposed within the button 320 and captures a needle hub retraction spring 324 between the needle hub 340 and a needle hub base 326. Specifically, the needle hub 340 is releasably secured to openings 338 of the needle hub base 326 by one or more safety spring retention latches 328, and wherein the needle hub retraction spring 324 is held in a compressed state between the needle hub 340 and the needle hub base 326.

The base 330 further comprises a cantilevered button retention latch 336 to capture the button 320 upon complete activation. In the exemplary embodiment shown, the device 300 has a circular shape, but is not limited thereto. The shape of the device can be configured in any number of shapes.

A line set 302 can then be attached to the upper housing 310 or base 330, or can be manufactured with the base 330, and can be connected to a medicament pump or other supply vessel. An adhesive liner 305 can be provided to cover an adhesive layer 304, such as a pressure sensitive adhesive (PSA), on the bottom of the device.

Figure 30:
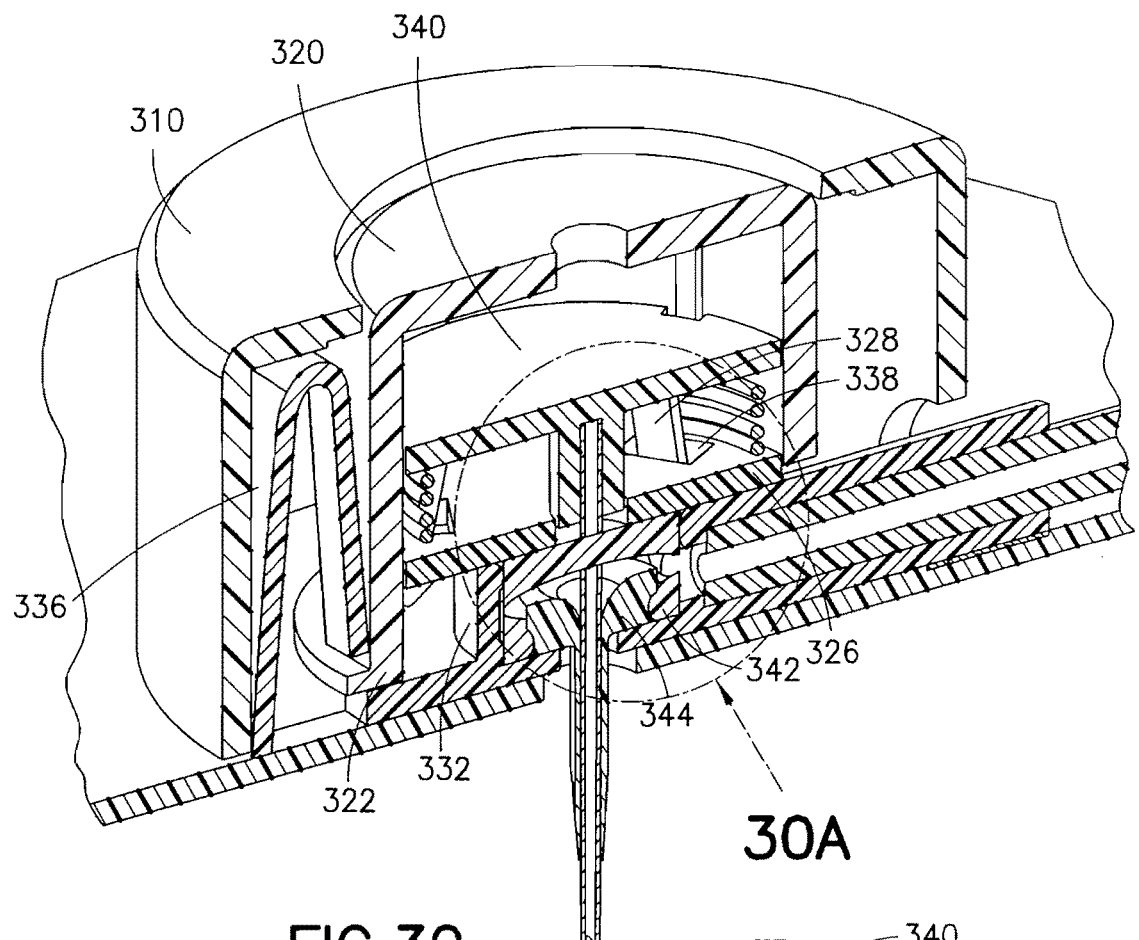
FIGS. 30 and 30A are enlarged cross-sectional views of the exemplary device of FIG. 28, illustrating the components thereof in greater detail after activation.
Figure 30A:
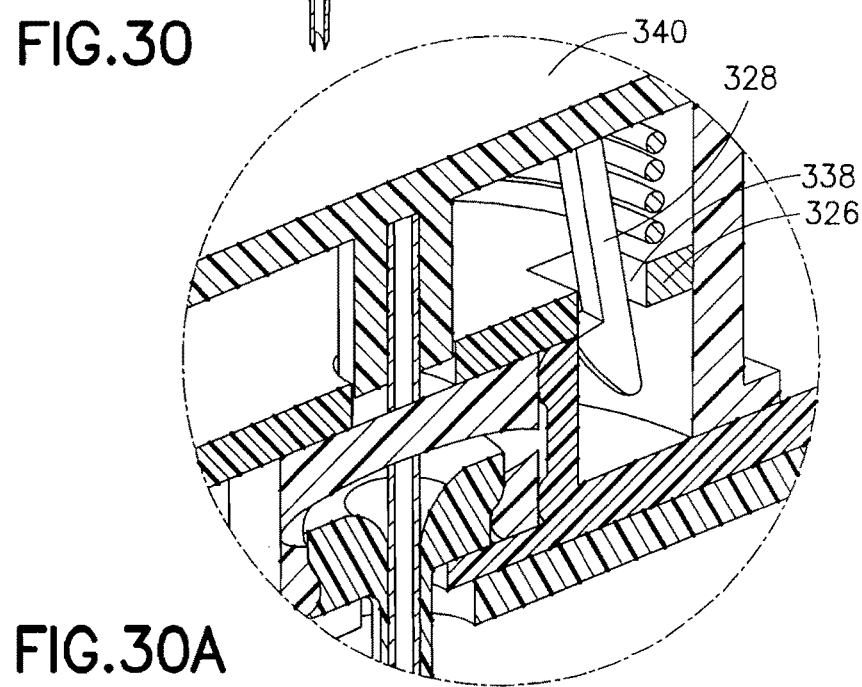
Figure 31:
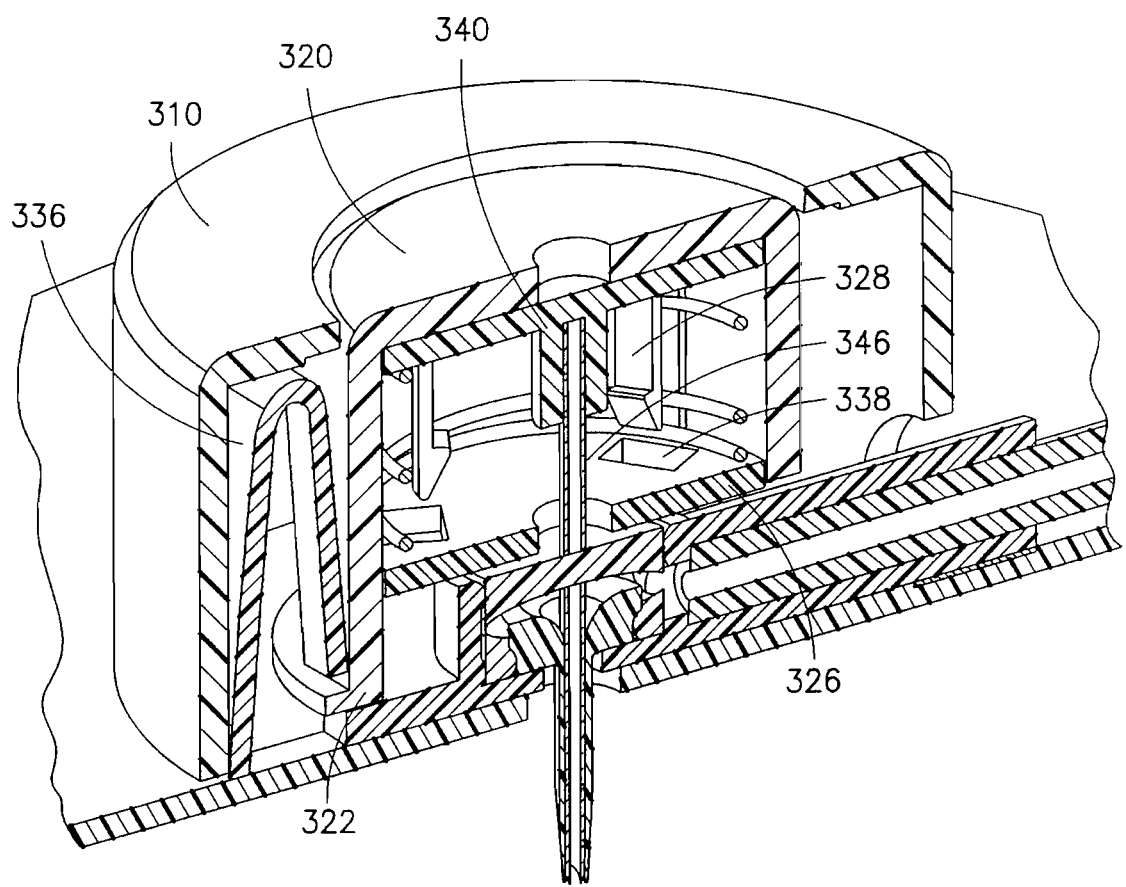
FIG. 31 is an enlarged cross-sectional view of the exemplary device of FIG. 28, illustrating the components thereof in greater detail after retraction.

In the exemplary fifth embodiment, when the button 320 is pressed toward the skin surface, the needle hub 340, catheter septum 342, catheter 344 and introducer needle 346 are moved downward, penetrating the patient's skin as depicted in FIG. 30. The shoulder 322 of the button 320 is captured in the down position by the button retention latches 336. At substantially the same moment, detents of the safety spring retention latches 328 contact and are deflected by the opening 332 of the base 330 as shown in the enlarged view of FIG. 30A. Once deflected, the needle hub 340 and introducer needle 346 are urged upward by the needle hub retraction spring 324 as shown in FIG. 31. The catheter septum 342 and catheter 344 remain in the base 330, either by the frictional force imparted by the seals 334 of opening 332 or by some other means of latching. The introducer needle 346 can be fully or partially withdrawn, depending on the shape of the spring 324.

In the fifth exemplary embodiment, a fluid path is created as shown in FIG. 31. Specifically, the catheter septum 342 comprises a number of septum perforations 348 as shown in FIG. 29. When the catheter septum 342 is positioned in the opening 332 of the base 330, the perforations 348 of the catheter septum 342 are sealed above and below the channel 336 by the seals 334. Fluid enters the base 330 via the lumen 306 of the tube set 302, passes through the channel 336 and into a cavity created by the seals 334 and outer body of the septum, then through the septum via the septum perforations 348, and enters the catheter 344 via the catheter perforations 352.

In an exemplary use, a user removes the adhesive liner from the lower surface to expose the adhesive layer 304 of the bottom of the device. In this position, the needle hub 340, catheter septum 342, catheter 344 and introducer needle 346 are retracted into the upper housing 310 and the button 320 is in an extended position. The device 300 can then be secured to an infusion site using the exposed adhesive layer 304. This ensures that the device 300 is fully contacting and adhesively secured to the skin surface before the user performs the deployment of the needle hub 340, catheter septum 342, catheter 344 and introducer needle 346. The user can then press the button 320 of the device 300 to drive the needle hub 340, catheter septum 342, catheter 344 and introducer needle 346 into position. Upon completed placement, the needle hub retraction spring is released and drives the needle hub 340 and introducer needle 346 into a retracted position. The needle hub 340 is driven upward against the upper interior of the button 320, such that the introducer needle tip is now drawn up inside of the catheter tip, thus shielding the needle tip. If not already connected, the tube 302 can then be connected to a pump or other medicament supply.

A lower profile can also be a function of catheter insertion. For example, an insertion operation can be used to actually reduce a profile of the assembly. In a sixth exemplary embodiment of the present invention, the device comprises another infusion set and insertion device integrated into a single unit, thereby again eliminating the need to carry any additional accessories and avoid the difficulty associated with loading the infusion set onto the insertion device at each use.

Figure 32:
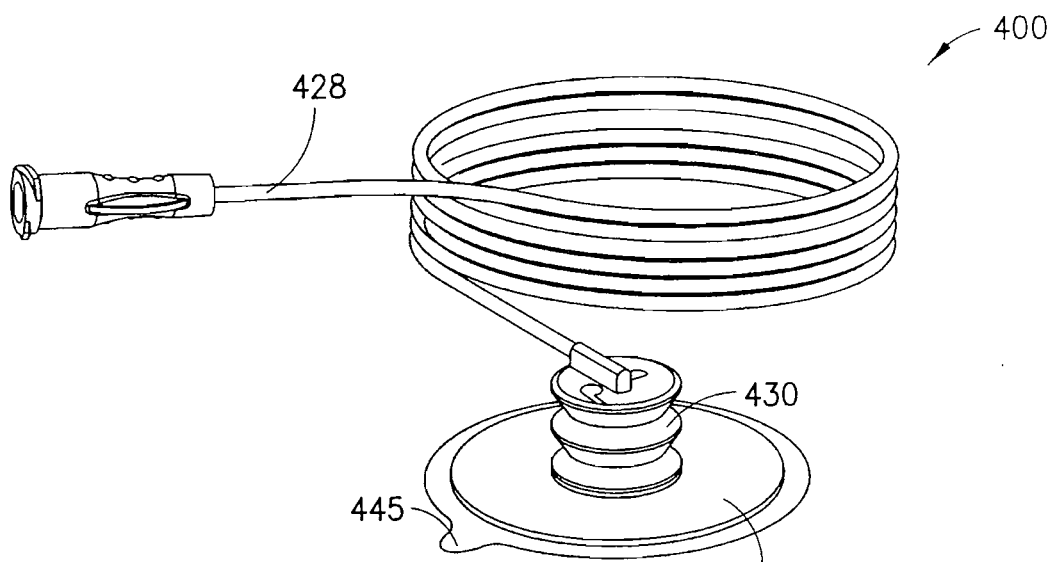
FIG. 32 is a perspective view of an exemplary device utilizing an integrated inserter and set in accordance with a sixth embodiment of the present invention before deployment.
Figure 33:
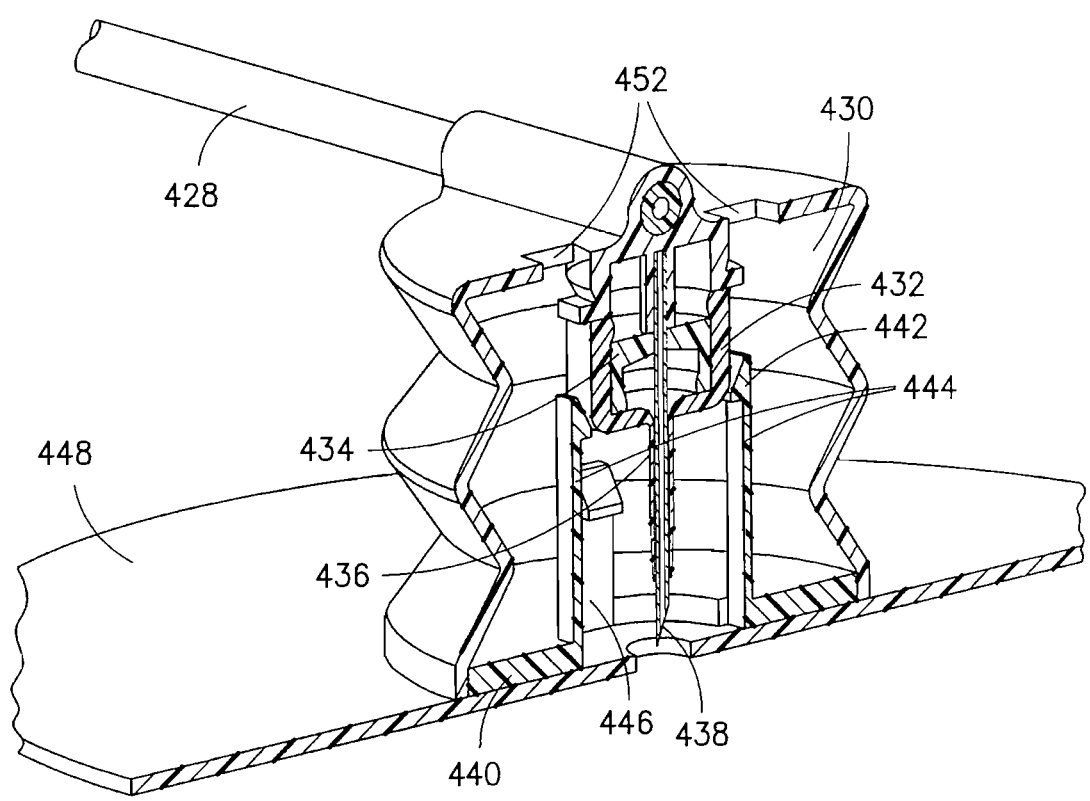
FIG. 33 is an enlarged cross-sectional view of the exemplary device of FIG. 32, illustrating the components thereof in greater detail prior to activation.

FIG. 32 is a view of an exemplary device 400 utilizing an integrated inserter and set in accordance with a sixth embodiment of the present invention and FIG. 33 shows the components therein in greater detail. The device 400 comprises an upper housing 430, secured to a base 440. As shown in FIG. 33, the upper housing 430 is constructed as a "bellows" shaped, collapsible body, wherein the shape allows the upper housing to be easily compressed into a smaller space. Within the upper housing 430, a catheter assembly 432 having a catheter septum 434, catheter 436 and introducer needle 438 are held in an up and retracted position between the upper housing 430 and detents 442 of body retention latches 444 of the base 440. The base 440 can further provide a catheter retention latch 446, wherein the latches 444 and 446 can surround a travel path of the catheter septum 434 to thereby guide, and subsequently capture, the catheter septum 434 during insertion of the catheter 436 and introducer needle 438. The upper housing 430 serves to contain most of the major components, and as a function of its bellows shape, can be compressed during insertion of the catheter 436 and introducer needle 438, and function as a spring to expand again toward its original shape for introducer needle 438 retraction after placement of the catheter 436.

A line set 428 can then be attached to the upper housing, or as shown in FIG. 33, can be manufactured with the upper housing 430, and can be connected to a medicament pump or other supply vessel. An adhesive liner 445 can be provided to cover an adhesive layer 448, such as a pressure sensitive adhesive (PSA), on the bottom of the device.

Figure 34:
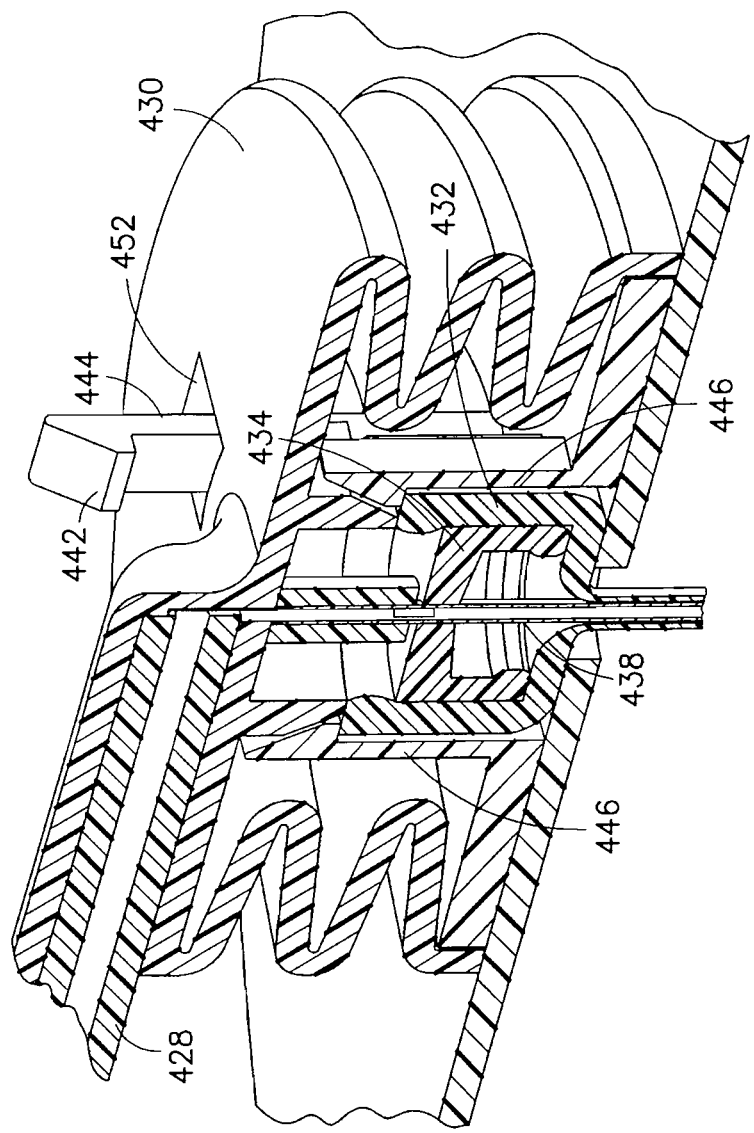
FIG. 34 is an enlarged cross-sectional view of the exemplary device of FIG. 32, illustrating the components thereof in greater detail after activation.

As shown in FIGS. 32-36 illustrating an exemplary use of the sixth embodiment, when the device is adhesively secured to a skin surface as shown in FIG. 33 and the upper housing 430 top surface is pressed toward the skin surface as shown in FIG. 34, it is compressed from its initial shape to a reduced shape. When pressed toward the skin surface, the upper housing 430 presses the catheter assembly 432 past the detents 442 of the body retention latches 444 of the base 440, and finally into the catheter retention latches 446 that surround the travel path of the catheter septum 434 during insertion of the catheter 436 and introducer needle 438.

Figure 35:
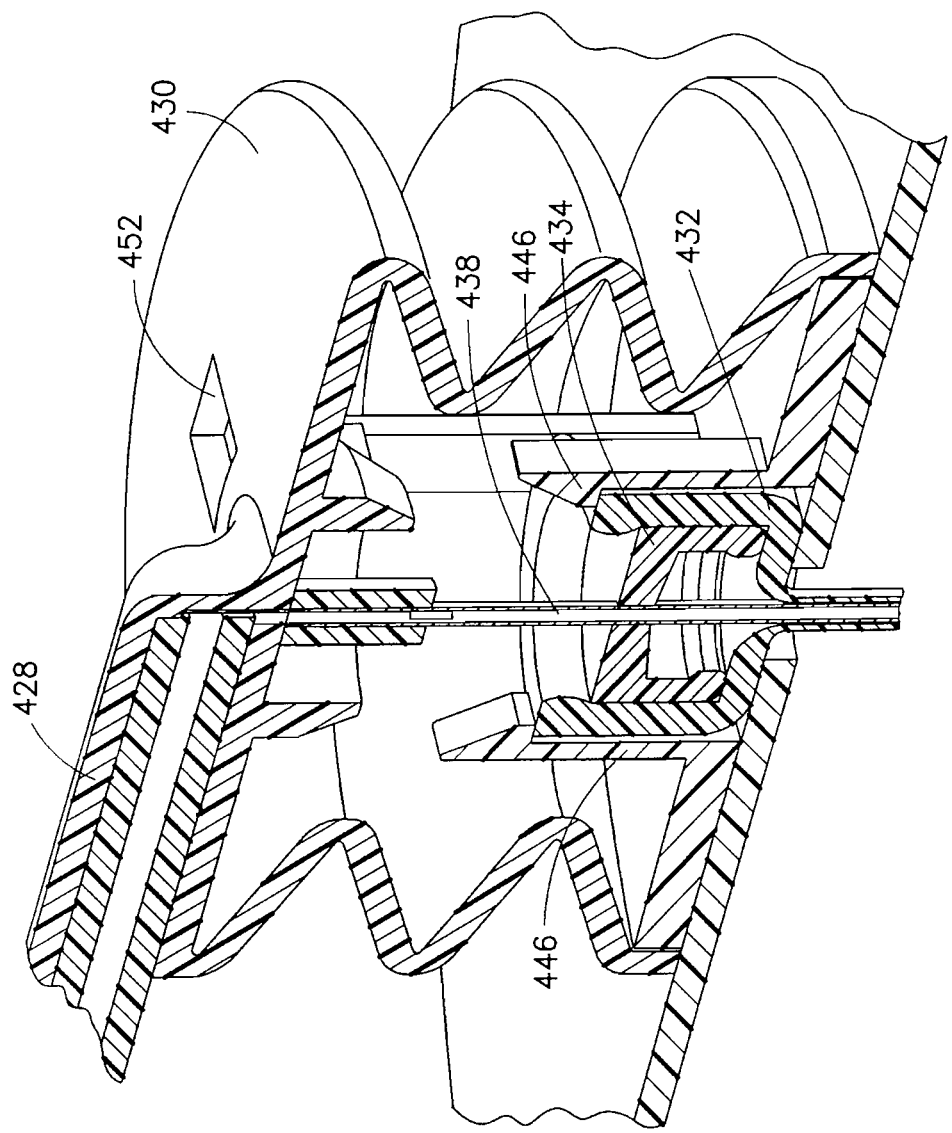
FIG. 35 is an enlarged cross-sectional view of the exemplary device of FIG. 32, illustrating the components thereof in greater detail after partial retraction.

Upon complete insertion of the catheter 436 and introducer needle 438, detents of the catheter retention latches 446 grasp and retain the catheter assembly 432 as shown in FIG. 34, maintaining the position of the catheter assembly in the down position, such that the catheter 436 and introducer needle 438 are at this time held in the patient's skin. However, once the pressure applied to the upper housing 430 is released as shown in FIG. 35, the integral spring nature of the upper housing 430 attempts to return the upper housing to its initial shape as shown. The catheter retention latches 446 continue to hold the catheter assembly 432 in position, but the introducer needle 438 is secured to the upper housing 430 and is slidably disposed within the catheter 436. Accordingly, as the upper housing 430 attempts to return to an original shape, the introducer needle 438 is retracted some distance within the catheter 436 which remains in position with the catheter assembly 432.

Figure 36:
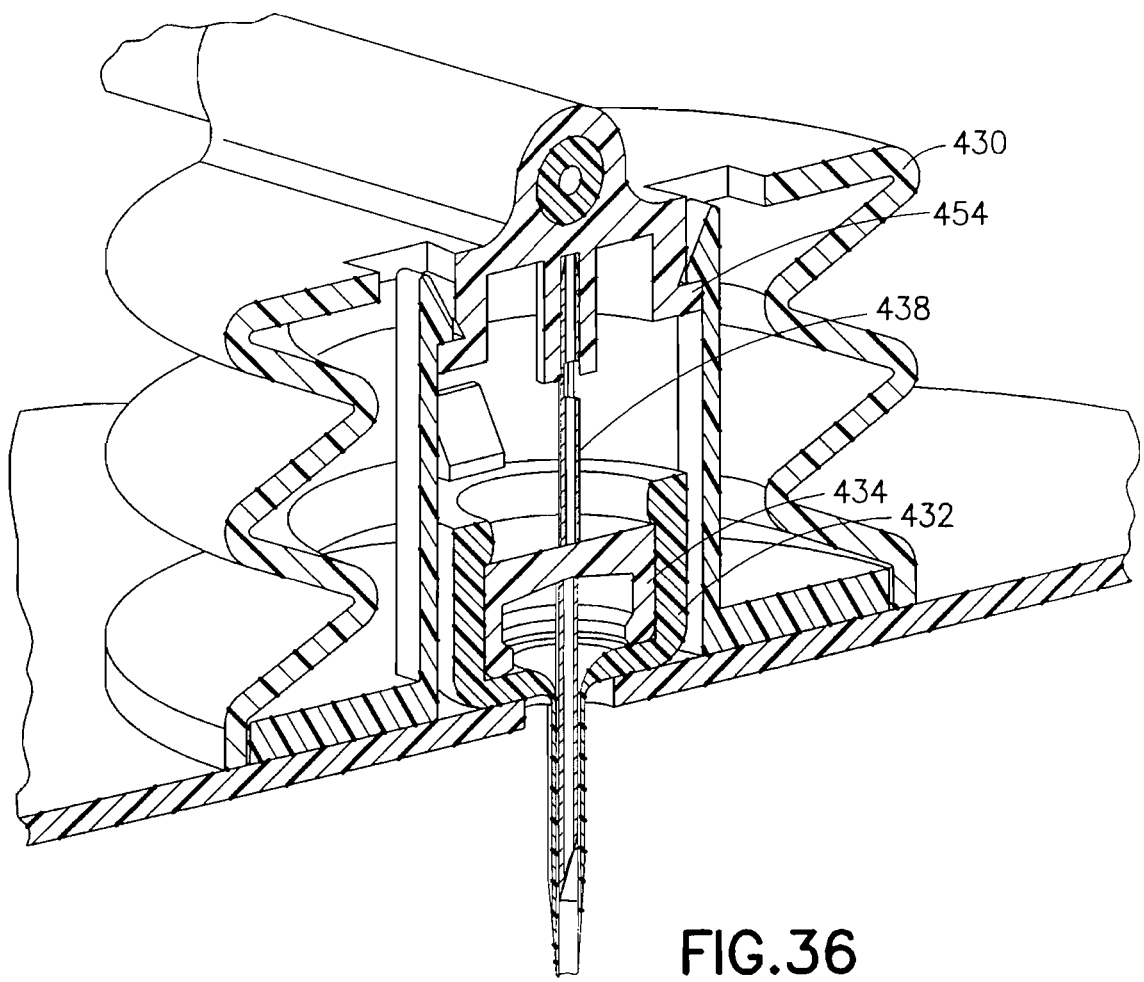
FIG. 36 is an enlarged cross-sectional view of the exemplary device of FIG. 32, illustrating the components thereof in greater detail after full retraction.

The upper housing 430 returns to an original shape to the extent permitted by the body retention latches 444. Specifically, the upper housing 430 comprises openings 452 through which the body retention latches 444 pass when the upper housing 430 is pressed downward. As the upper housing 430 attempts to return to an original shape, the detents 442 of the body retention latches 444 are captured by shoulders 454 to halt further upward motion of the upper housing 430 as shown in FIG. 36. This retracts the introducer needle 438 within the catheter 436, thus reducing the overall profile of the device, but containing the sharp introducer needle tip such that the needle tip will be unable to irritate the surrounding tissue.

The integral nature of features in the upper housing 430 and base 440 provide mechanisms without adding additional parts or assembly thereof. These mechanisms are provided by the body retention latches 444, catheter retention latches 446, and the integral spring action that results from the bellows shape of the upper housing 430. Elimination of parts also has potential to minimize the size of the device.

Figure 37:
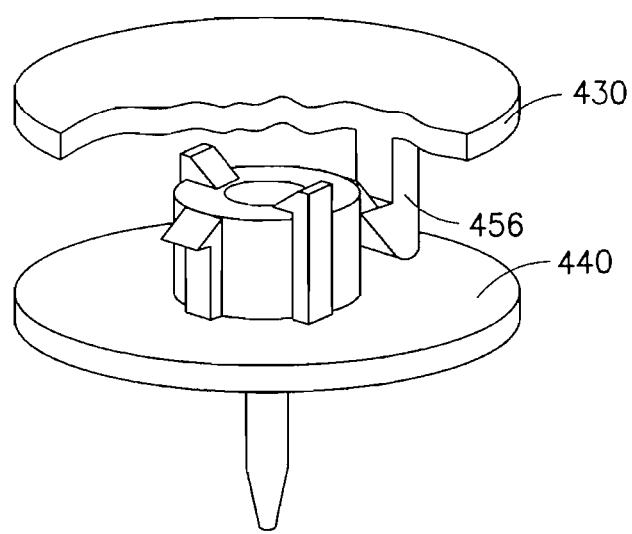
FIG. 37 is an enlarged cross-sectional view of the exemplary device of FIG. 32, illustrating the components thereof in greater detail after full retraction using another body retention embodiment.

In yet other exemplary embodiments, the upper housing 430 and openings 452 can be configured to conceal any protrusion by the body retention latches 444 so that they will not interfere with the user's fingers when they are in the protruded position shown in FIG. 34. For example, in another exemplary embodiment shown in FIG. 37, the body retention latches 456 can extend downward to capture lower body retention latches 458 thereby eliminating any protrusion of the latches during activation, while achieving the same effect as described above.

In a seventh exemplary embodiment of the present invention, the device comprises another infusion set and insertion device integrated into a single unit, thereby again eliminating the need to carry any additional accessories and avoid the difficulty associated with loading the infusion set onto the insertion device at each use.

Figure 38:
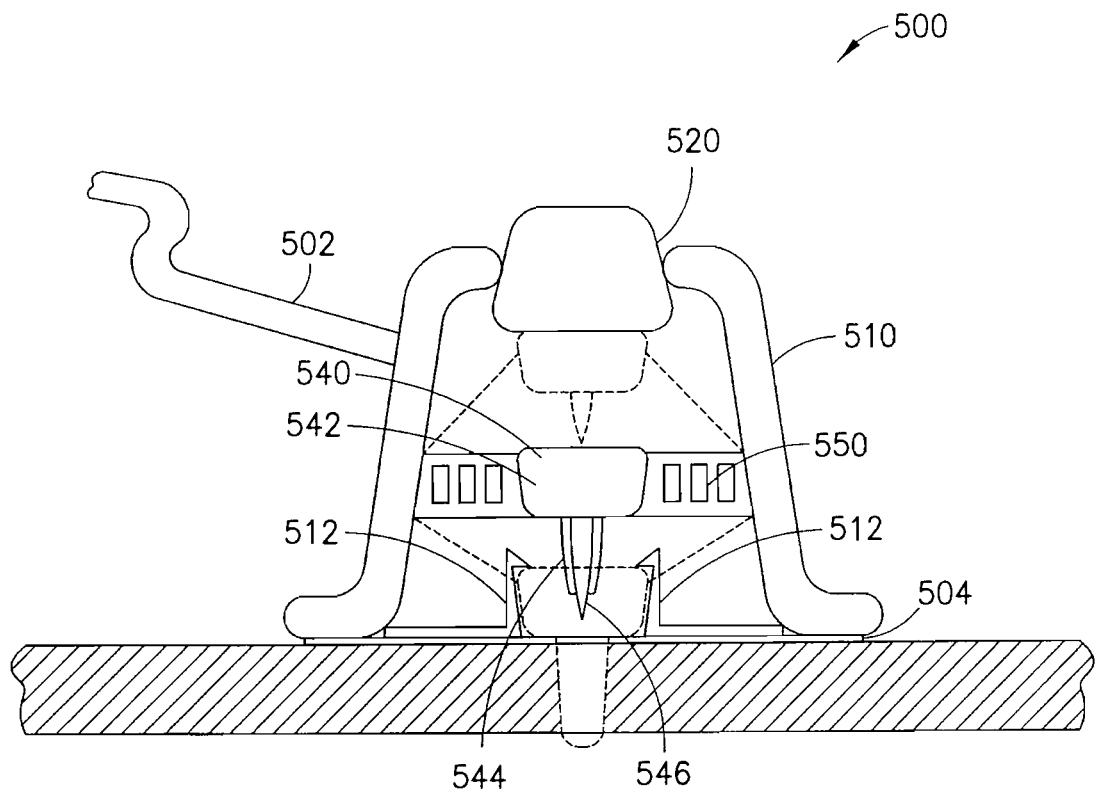
FIG. 38 is a cross-sectional view of an exemplary device utilizing an integrated inserter and set in accordance with a seventh embodiment of the present invention.
Figure 39:
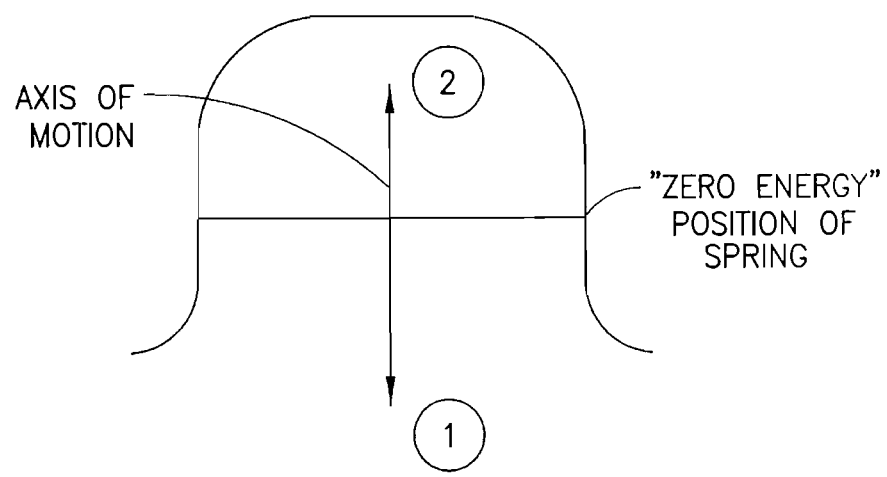
FIG. 39 is view illustrating an axis of motion of the exemplary device of FIG. 38 during activation.

FIG. 38 is a view of an exemplary device 500 utilizing an integrated inserter and set in accordance with a seventh embodiment of the present invention. The device 500 comprises an upper housing 510, from which a trigger 520 extends. Within the upper housing 510, a needle hub 540 having a catheter septum 542, catheter 544 and introducer needle 546 are held in an up and retracted position by the trigger 520. The catheter assembly 540 is flexibly connected to the upper housing 510 by a spring 550. Specifically, a flat coil spring, or similar spring, is provided to hold the catheter assembly 540 at a zero energy position within the upper housing as shown in FIG. 39. In doing so, the spring 550 permits an axis of motion of the catheter assembly 540 as shown in FIG. 39. A base of the housing 510 can comprise a latch 512 to capture the catheter septum 542 at a lower position, as described in greater detail below. An adhesive liner can be provided to cover an adhesive layer 504, such as a pressure sensitive adhesive (PSA), on the bottom of the device.

In current ballistic inserters, the inserter mechanism travels to one position after activation, and the introducer needle is then retracted with a subsequent step leaving an exposed needle point. However, the use of a pre-loaded, flat coil spring with a needle hub at a central opening and which is housed in a cylindrical barrel, perpendicular to the direction of motion, can achieve placement and retraction with a single step. Upon release, the spring can drive the introducer needle and catheter into a skin surface, whereupon the introducer needle retracts, or bounces back out of the skin surface due to the design and positioning of the flat coil spring. The introducer needle is retracted back into the cylindrical barrel housing, effectively removing the introducer needle and providing user safety since the introducer needle is not exposed during disposal.

Figure 40:
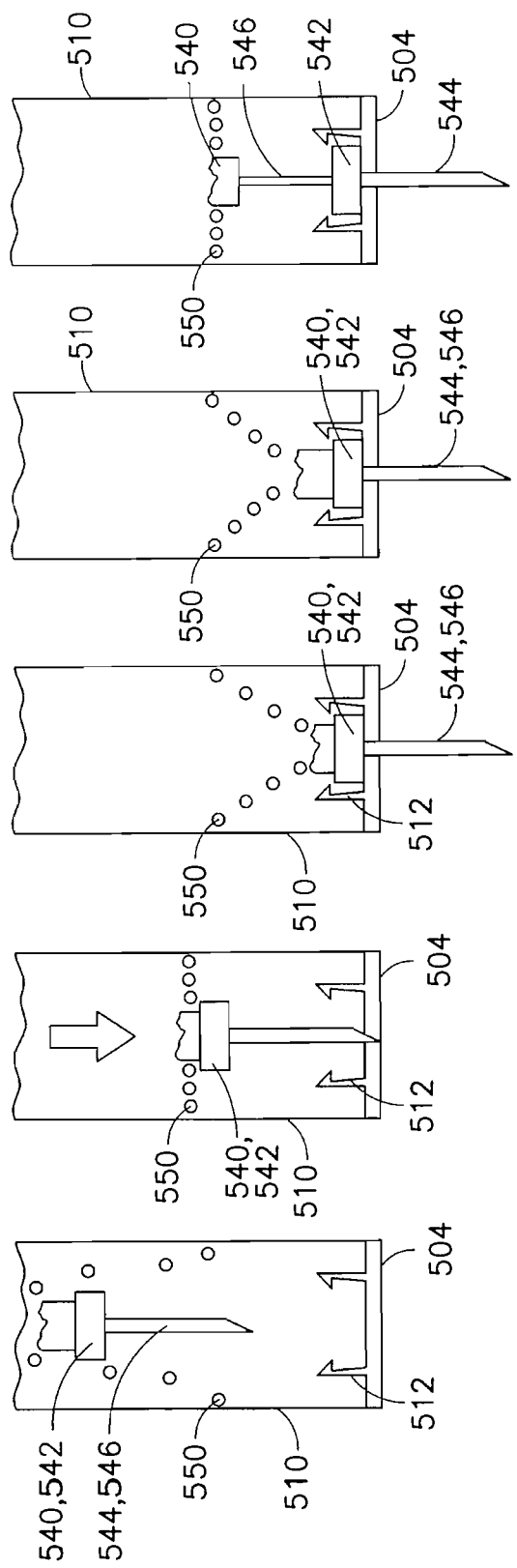
FIGS. 40A-40E are views illustrating a travel path of the exemplary device of FIG. 38 during activation.

Specifically, the spring 550 is secured between the upper housing 510 and the needle hub 540 at a zero energy position. The needle hub 540 is then releasably secured by the trigger 520 as shown in FIG. 40A. Construction of such a trigger 520 is well known to those skilled in the art and therefore, further description is not provided. The trigger 520 releasably holds the needle hub 540 in an up position, imparting stored energy to the spring 550. Upon release, the spring 550 urges the needle hub 540 toward the skin surface as shown in FIG. 40B. Specifically, upon release the needle hub 540 including the catheter septum 542, catheter 544 and introducer needle 546 are driven by the spring 550 toward the skin surface as shown in FIGS. 40C and 40D. Upon complete placement, the spring 550 urges the needle hub 540 and introducer needle 546 away from the skin surface, leaving the catheter septum 542 and catheter 544 in the down position as shown in FIG. 40E.

As shown in Equation (1) below, a sine wave can be used to represent the force of the spring in use,

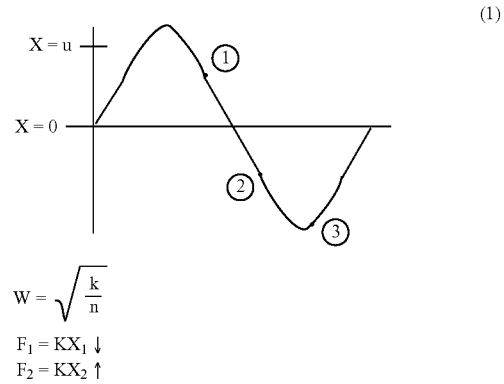

(1)

wherein at a position XU, the potential energy of the spring is at a maximum and force is at a minimum, at position X1 the force is toward the skin passing a zero energy position, at a position X2 the force is toward the skin engaging the skin surface and latches, and at a position X3, the force is turning away from the skin surface. The device will not work statically, and requires pre-positioning at a position XU and release to create momentum. Further, the spring will have momentum losses, which cannot exceed required insertion energy for proper operation. To ensure proper operation, Equation (2) below must be satisfied, $$\frac{MX_0^2}{2} \rangle\rangle \frac{KX_2^2}{2} - W_L \quad (2)$$

wherein WL=losses. The response of latches 512 at X2 must be faster than the bounce back at X3 due to impact. What will be observed can be shown in Equation (3) below, if latching is provided at insertion,

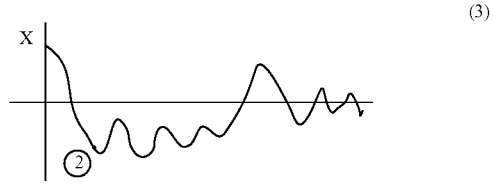

(3)

What will be observed can be shown in Equation (4) below, if no latching is provided at insertion,

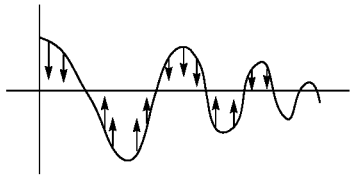 (4)

Attenuation due to energy losses in tissue insertion would cause decay in amplitude in both Equations (3) and (4). The embodiment can be configured to satisfy energy losses in any skin condition, and the latches 512 can be configured to respond as desired as illustrated in Equation (5) below, $$\text{Undamped:} \qquad (5)$$
$$X(t) = Xm\cos(\omega t + \phi)$$
$$X(t) = Xm\cos\omega t, \phi = 0$$

$$\text{Damped:}$$
$$X(t) = Xme^{-bt/2m}\cos(\omega' t + \phi)$$
$$X(t) = Xme^{-bt/2n}\cos(\omega' t), \phi = 0$$
$$\omega' t = \sqrt{\frac{k}{m} - \frac{b^2}{4m^2}}$$

In the exemplary embodiment shown, the device 500 has a circular shape, but is not limited thereto. The shape of the device can be configured in any number of shapes, but having a circular portion to permit coil spring operation. A line set 502 can then be attached to the device and can be connected to a medicament pump or other supply vessel. An adhesive liner can be provided to cover an adhesive layer 504, such as a pressure sensitive adhesive (PSA), on the bottom of the device.

In an exemplary use, a user removes the adhesive liner from the lower surface to expose the adhesive layer 504 of the bottom of the device. In this position, the needle hub 540, catheter septum 542, catheter 544 and introducer needle 546 are retracted into the upper housing 510 and held by the trigger 520. The device 500 can then be secured to an infusion site using the exposed adhesive layer 504. This ensures that the device 500 is fully contacting and adhesively secured to the skin surface before the user performs the deployment of the needle hub 540, catheter septum 542, catheter 544 and introducer needle 546. The user can then press the trigger 520 of the device 500 to release the spring 550 and drive the needle hub 540, catheter septum 542, catheter 544 and introducer needle 546 into position at the infusion site, and which can be held by latches 512 if provided. The continued spring 550 movement toward the zero-energy position drives the needle hub 540 and introducer needle 546 into a retracted position If not already connected, the tube 502 can then be connected to a pump or other medicament supply The seventh embodiment comprises an introducer needle and catheter mounted on the pre-loaded flat coil spring with a hub that is housed within a cylindrical barrel, perpendicular to the direction of motion. Upon activation, the spring releases and drives the introducer needle and catheter into the user's skin, whereupon the introducer needle retracts (i.e., bounces) back out of the skin, due to the design and positioning of the spring, and back into the cylindrical barrel housing, effectively removing the introducer needle and providing patient safety since there is no exposed needle.

Such a design provides a one-step motion for insertion and safety, with a simpler design having fewer parts and components. For example, neither inner barrel nor safety spring is required. In contrast, prior devices require a separate motion to remove the introducer needle and another motion to shield the device for safety. Utilizing a flat coil spring perpendicular to the direction of motion, placed in the correct barrel inner diameter location, enables the device to work in two directions in the same axis, therefore accomplishing insertion and then removal or retraction of the introducer needle.

The exemplary embodiments of the present invention described above incorporate hub-integrated insertion in which an introducer needle tip is retracted for comfort, but can remain for support of the catheter. Other exemplary embodiments of the present invention described above also incorporate hub-integrated insertion but wherein a flexible in-dwelling steel needle or catheter can be provided to remain in the skin and exhibit similar beneficial results. However, in other exemplary embodiments, a separate or non-integrated inserter can also be used to provide a very low profile hub and set. In this case, the introducer needle and/or driving mechanism can remain with the separate, removable inserter.

In an eighth exemplary embodiment of the present invention, the device comprises a single-use infusion set and insertion device preassembled into a single unit, thereby again eliminating at least the need to carry and assemble separate accessories, and avoiding the difficulty associated with loading the infusion set into the insertion device at each use.

FIGS. 41-43 are views of an exemplary device 600 utilizing an inserter and infusion set in accordance with a third embodiment of the present invention. The device 600 comprises an insertion device 610, from which a user push button 620 extends. The insertion device 610 further contains an infusion set 650 at a distal end for placement at an infusion site. During placement, a catheter 630 can be extended from a bottom surface of a set hub 640 of the infusion set 650 during activation of the insertion device 610. FIG. 44 is a cross-sectional view of the exemplary device of FIG. 41, illustrating the components thereof in greater detail.

As shown in FIG. 41, the insertion device 610 contains the infusion set 650 at a distal end for placement. An adhesive pull liner 635 covering an adhesive layer 636 can be provided to seal and secure the distal end of the insertion device 610. The insertion device 610 further comprises an opening at a side surface in which the push button 620 is disposed. The push button 620 is configured to slidably travel substantially parallel to a skin surface from an extended position to a substantially flush position. In doing so, the push button 620 is configured to release a driving mechanism of the insertion device 610 and drive a catheter holder 612 into an infusion set 650 for placement at an infusion site.

The core, independent catheter holder 612, is deployed with the catheter 630 into the hub 640, which is secured to the skin surface. In an exemplary embodiment of the present invention, an insertion spring mechanism (not shown) is disposed within the insertion device in a loaded state such that the movement of the push button 620 releases the spring and deploys the independent catheter holder 612. Construction of such a driving mechanism is well known to those skilled in the art and therefore, further description is not provided.

Figure 45:
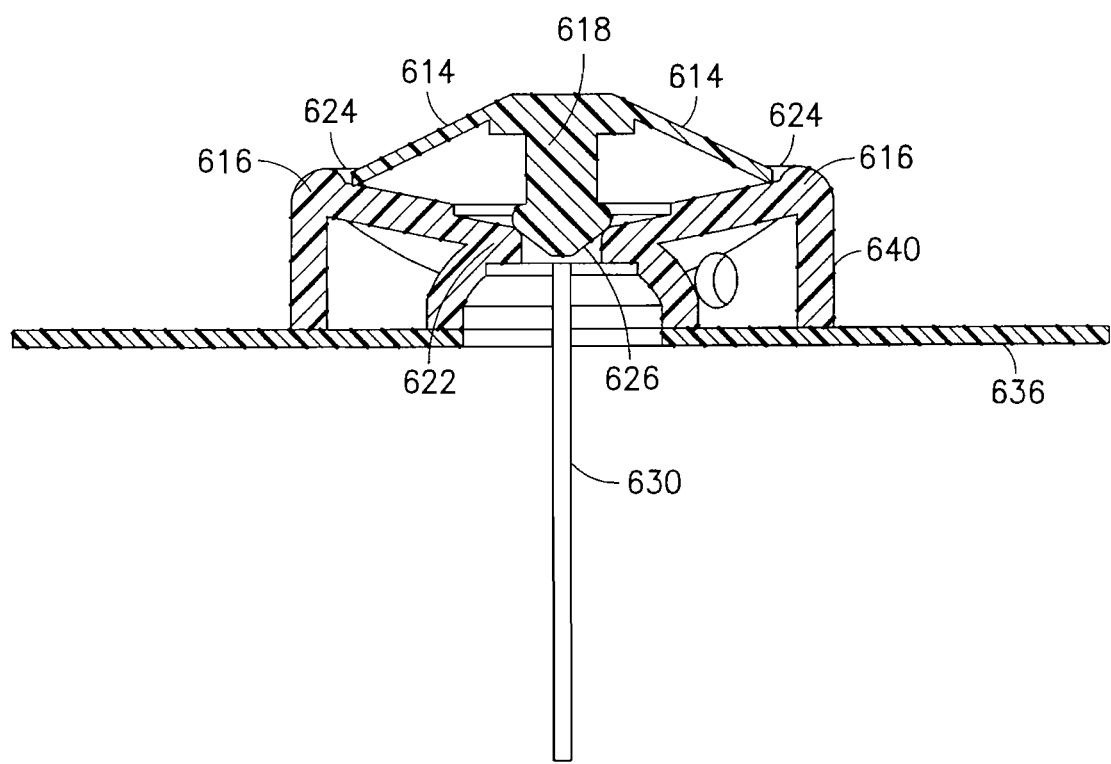
FIG. 45 is a cross-sectional view of the exemplary set of FIG. 41, illustrating the components thereof in greater detail.

As shown in FIG. 44, the insertion device 610 contains the independent catheter holder 612 in a position above the infusion set 650. As shown in greater detail in FIG. 45, the independent catheter holder 612 comprises an outer flexible or resilient member 614 surrounding and supporting a main body 618 and catheter 630. When activated, the independent catheter holder 612, outer flexible or resilient member 614, main body 618 and catheter 630 are driven downward into the infusion site. The outer flexible or resilient member 614 is centered and held in position by an opening 616 in the hub 640. The opening 616 can comprise a shoulder or detent 624 to assist in capturing and holding the outer flexible or resilient member 614 once in position. The main body 618 has a rounded distal end 626 to self-align with an opening 622 in the hub 640. The catheter 624 is aligned and positioned within the hub 640, but is isolated from movement by the engagement between the flexible or resilient member 614 and the opening 616 in the hub 640.

The hub 640 further comprises a tube connection 642 which can be connected with a medicament pump or other supply vessel. The adhesive liner 635 can be provided to cover the adhesive layer 636, such as a pressure sensitive adhesive (PSA), on the bottom of the hub 640.

FIGS. 46A-46F are views of the exemplary device 600 of FIG. 41 in use. In a first step of FIG. 46A, a user removes the adhesive liner 635 from the lower surface to expose the adhesive layer 636 of the bottom of the device 600. The hub 640 of the device 600 can then be secured to an infusion site using the exposed adhesive layer 636 as shown in FIG. 46B. This ensures that the hub 640 of the device 600 is fully contacting and adhesively secured to the skin surface before the user performs the deployment of the catheter 630. The user can then press the button 620 of the device 600 to insert the introducer needle and catheter, or a self-placing, in-dwelling catheter 630 in a single motion as shown in FIG. 46C. The insertion device 610 can then be removed and the tube 642 can then be connected to an insulin infusion pump or other medicament supply 644 as shown in FIGS. 46D-46F.

In the eighth exemplary embodiment of the present invention, the user can attach the complete device to the skin surface and then deploy the independent catheter holder and catheter, preventing any bunching of the adhesive when attached as well as ensuring that the set hub is fully contacting and adhesively secured to the skin before the catheter is inserted. This also ensures that the catheter is inserted at the correct depth.

The exemplary device further provides a "floating catheter" feature of the independent catheter holder 612 wherein the catheter assembly is flexibly or resiliently suspended or supported in the hub to dampen motion due to body movement or accidental bumps and/or tubing tugs. The device uses an automatic method of deployment as the user only needs to push the button of the device to insert the catheter.

As noted above, in a conventional system, an introducer needle, catheter, and adhesive, are all deployed at substantially the same time and during such ballistic insertion, there is a high-speed contact of the adhesive pad while the introducer needle and the catheter are being inserted which may result in partially inserted catheters and/or incomplete adhesion. The exemplary eighth embodiment of the present invention eliminates the potential of partial insertion of the catheter and/or incomplete adhesion, since the system and method first ensures that the hub of the set is fully contacting and adhesively secured to the skin surface and then performs the deployment of the catheter. Further, the catheter assembly is configured to "float" in the hub, which serves to dampen motion due to body movement or accidental bumps and/or tubing tugs.

The exemplary eighth embodiment of the present invention significantly reduces the steps required to insert the infusion set since the user is not required to load the infusion set into the inserter device. Further, the flexible catheter including sharpened tip is hidden from the user prior to use and insertion, which makes the device more safe and appealing to users who are uncomfortable with needles.

As noted above, the device is configured for the user to attach the device to the skin surface in a first step, then deploy the introducer needle in a second step, thereby preventing any bunching of the adhesive when attached as well as ensuring that the set hub is fully contacting the skin before the introducer needle is inserted. This also ensures that the catheter is inserted at the correct depth. Further, the catheter is configured to "float" in the hub which serves to dampen motion due to body movement and/or accidental humps to the hub and/or tubing tugs.

In exemplary embodiments of the present invention, the housings, hubs and other elements can be constructed of molded plastic materials, polycarbonate, thermoplastic polymers such as polyethylene terephthalate (PET and PETG), or similar materials. Springs and introducer needles can be constructed of stainless steel or similar materials. Although the embodiments described above are dimensioned and configured for subcutaneous injections, they can also be used for other types of injections, such as intradermal or intramuscular injections.

Further, one or more of the exemplary embodiments of the present invention can be provided with a skin contacting adhesive layer and backing. Precise insertion is achieved by first securing the infusion set hub to the infusion site via the adhesive, which permits the user to activate the inserter or place the catheter as described above at the proper alignment. In doing so, the introducer needle is driven into the skin surface at a controlled high rate of speed to minimize the risk of tenting at introducer needle insertion. Further, the adhesive at or very near the insertion site secures the skin surface and minimizes tenting of the skin surface during insertion.

In current infusion sets which deliver insulin or other medicament to the subcutaneous layer, the catheter is not isolated from any undesired outside forces, which may cause pain when translated to the catheter which then moves within the skin. Also, other devices face problems of premature or unintended catheter removal when the device is bumped, if the catheter is not isolated from the outside forces. In the exemplary embodiments of the present invention, the catheter can isolated from outside forces by at least one flexible or resilient feature.

Still further, many commercial infusion sets require the use of a separate inserter. In the exemplary hub-integrated insertion embodiments of the present invention described herein, the user does not have to carry a separate inserter or load the infusion set into the inserter. The integrated system allows the user freedom from carrying and loading a separate inserter, resulting in improved convenience and simpler operation.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. An infusion device, comprising an inserter that can insert a catheter into a skin surface, comprising:
   an infusion device housing, comprising a catheter and a driver for placing said catheter into a skin surface; and
   an infusion device base, comprising at least one adhesive layer for releasably securing said infusion device base with said skin surface; and
   an introducer needle and a catheter septum, wherein said driver comprises a rotating needle hub fixedly attached to said introducer needle, the driver configured to rotate within said infusion device housing by a force applied by a first spring and press said introducer needle and said catheter into said skin surface; wherein said rotating needle hub is configured to further rotate within said infusion device housing by a force applied by said first spring and retract said introducer needle from said catheter; said first spring being a torsion spring extending through said rotating needle hub to permit linear translation of said rotating needle hub relative to the torsion spring as the torsion spring rotates the rotating needle hub.

2. An infusion device as claimed in claim 1, wherein said driver comprises:
   a rotating cam ring configured to rotate within said infusion device housing and press said catheter into said skin surface.

3. An infusion device as claimed in claim 1, wherein:
   said base comprises a septum opening for slidably receiving said catheter septum, said septum opening comprising a fluid path opening;
   said catheter septum comprises a fluid path opening; and
   said catheter comprises a fluid path opening, wherein said fluid path openings are aligned when said introducer needle and said catheter are inserted into said skin surface.

4. An infusion device as claimed in claim 1, wherein said driver comprises:
   a push button configured to travel substantially parallel to said skin surface and release said catheter and insert said catheter into said skin surface.

5. A method of placing an infusion device, comprising the steps of:
   placing an infusion device base upon an infusion site and activating a driver to insert a catheter into said infusion site,
   wherein said driver comprises a rotating needle hub fixedly attached to at least one of a catheter and an insertion needle and configured to rotate within an infusion device housing by a rotation force applied by a first spring to insert the at least one catheter or introducer needle into said infusion site and to retract the rotating needle hub by a further rotation force applied by the first spring; said first spring being a torsion spring extending through said rotating needle hub to permit linear translation of said rotating needle hub relative to the torsion spring as the torsion spring rotates the rotating needle hub.

6. A method of placing an infusion device as claimed in claim 5, comprising the steps of:
   activating said driver to retract said introducer needle, wherein said driver comprises a rotating member to retract said introducer needle from said catheter.

7. The infusion device of claim 1, wherein a direction of rotation of the rotating needle hub is parallel to a direction of rotation of the torsion spring.

8. The method of placing an infusion device as claimed in claim 5, wherein a direction of rotation of the rotating needle hub is parallel to a direction of rotation of the torsion spring.

* * * * *